US010677711B2

(12) United States Patent
Herzog et al.

(10) Patent No.: US 10,677,711 B2
(45) Date of Patent: Jun. 9, 2020

(54) METHOD AND APPARATUS FOR AUTOMATED WHOLE BLOOD SAMPLE ANALYSES FROM MICROSCOPY IMAGES

(71) Applicant: Abbott Point of Care, Inc., Princeton, NJ (US)

(72) Inventors: David Herzog, Warrington, PA (US); Zhizhou Wang, Princeton, NJ (US); Stephen C. Wardlaw, Lyme, CT (US); Min Xie, Plainsboro, NJ (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 16/524,422

(22) Filed: Jul. 29, 2019

(65) Prior Publication Data

US 2019/0346362 A1 Nov. 14, 2019

Related U.S. Application Data

(60) Continuation of application No. 15/487,870, filed on Apr. 14, 2017, now Pat. No. 10,365,203, which is a
(Continued)

(51) Int. Cl.
*G06K 9/00* (2006.01)
*G01N 21/03* (2006.01)
(Continued)

(52) U.S. Cl.
CPC ..... *G01N 15/1475* (2013.01); *G01N 21/5907* (2013.01); *G01N 21/6458* (2013.01);
(Continued)

(58) Field of Classification Search
USPC ............... 382/100, 103, 106–107, 128–129, 382/133–134, 162, 168, 173, 181, 203,
(Continued)

(56) References Cited

U.S. PATENT DOCUMENTS

| 4,125,828 A | 11/1978 | Resnick et al. |
| 4,175,860 A | 11/1979 | Bacus |

(Continued)

FOREIGN PATENT DOCUMENTS

| CN | 101464245 A | 6/2009 |
| EP | 0259833 A2 | 3/1988 |

(Continued)

OTHER PUBLICATIONS

Burges, "A Tutorial on Support Vector Machines for Pattern Recognition", Data Mining and Data Knowledge Discovery 2: 121-167, 1998.

(Continued)

*Primary Examiner* — Seyed H Azarian
(74) *Attorney, Agent, or Firm* — Getz Balich LLC

(57) ABSTRACT

An apparatus and a method for identifying at least one type of white blood cell (WBC) within a whole blood sample is provided. The method includes: adding at least one colorant to the sample; providing at least one fluorescent excitation light and at least one transmission light; receiving both light fluorescing from and transmitted through the sample and producing signals representative thereof; creating at least one image of the sample using the signals; identifying WBCs within the sample image; quantitatively analyzing at least some of the identified WBCs within the image, including determining one or more quantitative values; and identifying at least one type of WBC from the identified WBCs using the quantitative values.

17 Claims, 15 Drawing Sheets

(8 of 15 Drawing Sheet(s) Filed in Color)

Related U.S. Application Data division of application No. 13/204,415, filed on Aug. 5, 2011, now Pat. No. 10,203,275.

(60) Provisional application No. 61/371,020, filed on Aug. 5, 2010.

(51) Int. Cl.

| | |
|---|---|
| *G01N 15/14* | (2006.01) |
| *G01N 21/59* | (2006.01) |
| *G01N 21/64* | (2006.01) |
| *G01N 33/50* | (2006.01) |
| *G01N 33/49* | (2006.01) |
| *G01N 15/00* | (2006.01) |

(52) U.S. Cl.
CPC ......... *G01N 33/49* (2013.01); *G01N 33/5094* (2013.01); *G01N 2015/008* (2013.01)

(58) Field of Classification Search
USPC ....... 382/219, 224, 232, 254, 274, 276, 286, 382/291, 305, 312; 435/34, 287.1; 436/165; 359/396
See application file for complete search history.

(56) References Cited

U.S. PATENT DOCUMENTS

| | | | |
|---|---|---|---|
| 4,307,376 A | 12/1981 | Miller et al. | |
| 4,581,223 A | 4/1986 | Kass | |
| 5,123,055 A | 6/1992 | Kasdan | |
| 5,436,978 A | 7/1995 | Kasdan | |
| 6,169,816 B1* | 1/2001 | Ravkin | G01N 15/1475 382/128 |
| 6,251,615 B1 | 6/2001 | Oberhardt | |
| 7,009,894 B2 | 3/2006 | Mukker et al. | |
| 8,218,883 B2* | 7/2012 | Ohkubo | G06F 16/50 382/232 |
| 2001/0050810 A1* | 12/2001 | Lorincz | G01N 1/30 359/396 |
| 2002/0055178 A1* | 5/2002 | Wardlaw | G01N 15/05 436/165 |
| 2006/0024756 A1 | 2/2006 | Tibbe et al. | |
| 2006/0110283 A1 | 5/2006 | Fish | |
| 2007/0243317 A1 | 10/2007 | Du Bois et al. | |
| 2008/0019584 A1 | 1/2008 | Lindberg et al. | |
| 2008/0170772 A1 | 7/2008 | Lindberg et al. | |
| 2009/0011518 A1 | 1/2009 | Lindberg | |
| 2009/0239257 A1* | 9/2009 | Levine | G01N 15/1475 435/34 |
| 2010/0273244 A1* | 10/2010 | Wardlaw | B01L 3/508 435/287.1 |
| 2012/0217605 A1 | 8/2012 | Kunikiyo | |

FOREIGN PATENT DOCUMENTS

| | | |
|---|---|---|
| WO | 9945384 A1 | 9/1999 |
| WO | 9945385 A1 | 9/1999 |
| WO | 2009117664 A2 | 9/2009 |

OTHER PUBLICATIONS

Walsh, "Introduction to Bayesian Analysis", Lecture Notes for EEB 596z, copyright B. Walsh, 2002.
Weston, "Support Vector Machine (and Statistical Learning Theory) Tutorial", NEC Labs America.
Moore, "Support Vector Machines", School of Computer Science, Carnegie Mellon University, Copyright 2001, 2003.
Noriega, "Multilayer Perceptron Tutorial", School of Computing, Staffordshire University, Beaconside Staffordshire ST18 0DG, Nov. 2005.
Ray et al., "Spectroscopic and Structural Studies on Adsorption of Azo Dye in Cationic Langmuir-Blodgett Films", The Chemical Society of Japan, Bull. Chem. Soc. Jpn., 75, 1943-1501 (2002).
Sabino et al., "A texture approach to leukocyte recognition", Real-Time Imaging, vol. 10, No. 4, Aug. 2004.
Sinha et al., "Blood Cell Segmentation using EM algorithm", Proceedings of the Third Indian Conference on Computer Vision, Graphics & Image Processing, Dec. 2002.
Katz, "Image Analysis and Supervised Learning in the Automated Differentiation of White Blood Cells from Microscopic Images", Master Thesis, 2000,http://citeseerx.ist.psu.edu/viewdoc/summary?doi=10.1.1.31.9085.
Kovalev et al., "Robust Recognition of White Blood Cell Images", Proceedings of 13th International Conference on Pattern Recognition, vol. 4, 1996, pp. 371-375.
Chen et al., "Cell classification by moments and continuous wavelet transform methods", International Journal of Nanomedicine, 2007, 2(2): 181-189.
Khashman A., "IBCIS: Intelligent blood cell identification system", Progress in Natural Science, 2008; 18: 1309-1314.
Paddock et al., "Imaging modes", Microscopy U, 2009; 1-5.
Spring, K., "Fluorescence microscopy", Encyclopedia of Optical Engineering, 2003; 548-555.
Zhang et al., "Transmittance measurements for filters of optical density between one and ten", Applied Optics, 1997; 36(34):8889-8895.
Mircic et al., "Application of neural network for automatic classification of leukocytes", IEEE, 2006; 141-144.
Borzini et al., "Mircodroplet fluorochromatic assay for the enumeration of white cells (WBCs) in WBC-reduced blood components: validation and application for evaluating newly developed WBC-reduction filters", Transfusion, 1997; 37:601-606.

* cited by examiner

|  | Lymphocyte | Neutrophil | Eosinophil | Monocyte |
|---|---|---|---|---|
| Composite Image | FIG. 5A | FIG. 5B | FIG. 5C | FIG. 5D |
| FL Red | FIG. 6A | FIG. 6B | FIG. 6C | FIG. 6D |
| FL Green | FIG. 7A | FIG. 7B | FIG. 7C | FIG. 7D |
| TL Blue OD | FIG. 8A | FIG. 8B | FIG. 8C | FIG. 8D |
| Cell Mask | FIG. 9A | FIG. 9B | FIG. 9C | FIG. 9D |

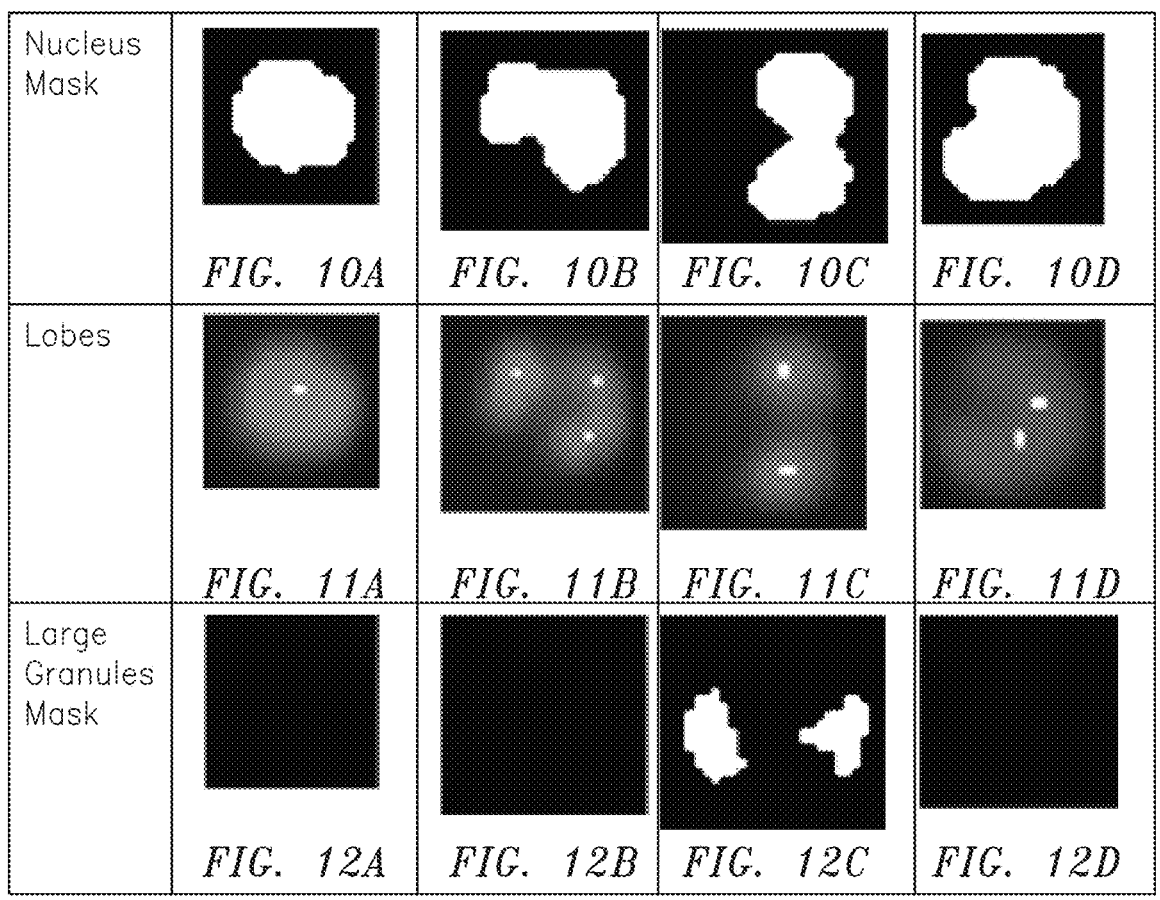
FIG. 10A  FIG. 10B  FIG. 10C  FIG. 10D
FIG. 11A  FIG. 11B  FIG. 11C  FIG. 11D
FIG. 12A  FIG. 12B  FIG. 12C  FIG. 12D
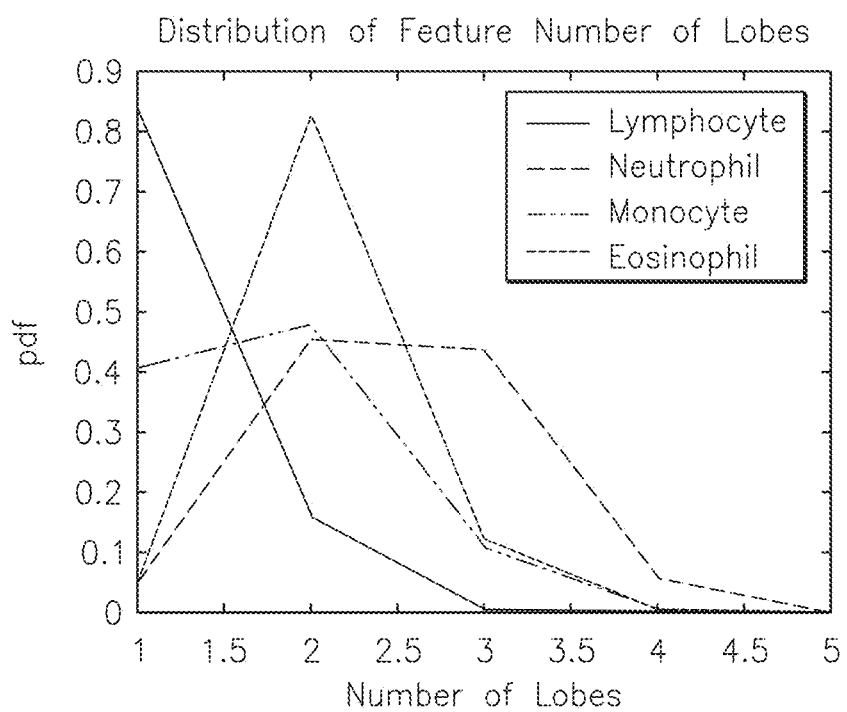
FIG. 13

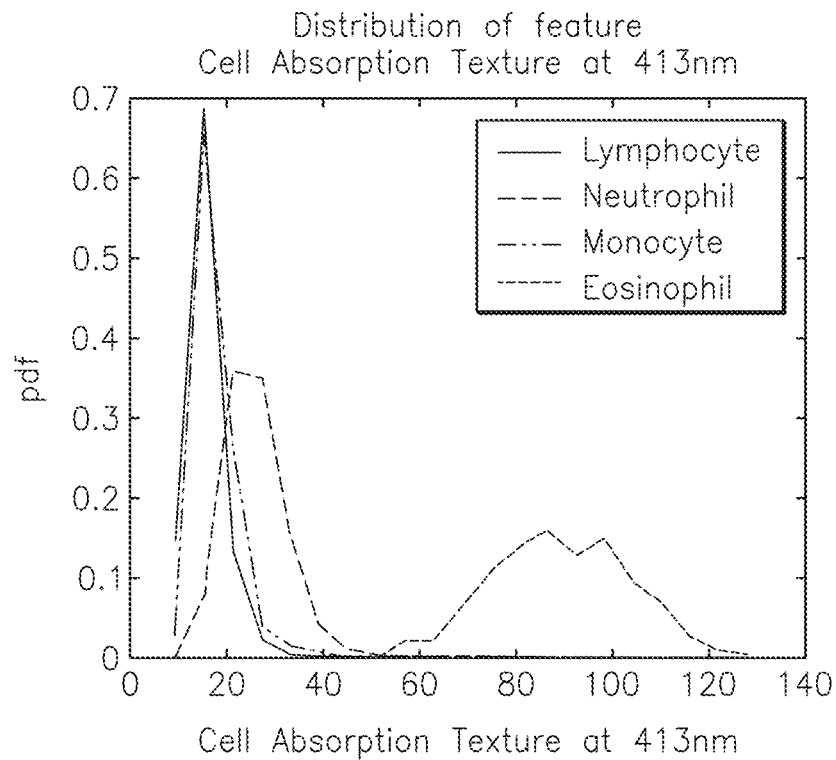

FIG. 29

| Cell Type | Dominant Distinguishing Cell Features |
|---|---|
| Lymphocyte | Number of Lobes<br>Cell Area<br>Ratio of Nucleus<br>Nucleus Shape |
| Neutrophil | Number of Lobes<br>Cell Area<br>Ratio of Nucleus<br>Nucleus Shape |
| Monocyte | Number of Lobes<br>Cell Area<br>Ratio of Nucleus |
| Eosinophil | Average Cell Absorption at a given wavelength<br>Cell Absorption Texture at a given wavelength<br>Ratio of Large Granules |

FIG. 30

METHOD AND APPARATUS FOR AUTOMATED WHOLE BLOOD SAMPLE ANALYSES FROM MICROSCOPY IMAGES

This application is a continuation of U.S. patent application Ser. No. 15/487,870 filed Apr. 14, 2017, which is a divisional of U.S. patent application Ser. No. 13/204,415 filed Aug. 5, 2011, which is entitled to the benefit of and incorporates by reference essential subject matter disclosed in the U.S. Provisional Patent Application Ser. No. 61/371,020, filed Aug. 5, 2010.

BACKGROUND OF THE INVENTION

1. Technical Field

The present invention relates to methods and apparatus for performing analyses on whole blood samples from microscopy images in general, and to automated version of the same in particular.

2. Background Information

Medical diagnostics often include analyses of a whole blood sample from a patient. One of the more popular diagnostics is a complete blood count (referred to as a "CBC"), which is a suite of tests that may include, in addition to the enumeration of the cellular components, red blood cell metrics, reticulocyte counts, and a leukocyte differential count ("LDC"; sometimes referred to as a "white blood cell differential"), which is the identification and enumeration of the types of white blood cells (WBCs) present in the blood sample.

Historically, the differential aspects of the CBC have been performed using separate methods from those used for enumeration. For example, the LDC portion of a CBC historically has been performed by smearing a small amount of undiluted blood on a slide, staining the dried, fixed smear, and examining the smear under a microscope. Reasonable results can be gained from such a smear, but the accuracy and reliability of the data depends largely on the technician's experience and technique. Blood smears are problematic for several reasons; e.g., the cells must be killed and fixed, which process precludes many types of supravital stains and analyses whose results depend upon living cells, and blood smears are labor intensive, cost prohibitive, and time consuming. For at least these reasons, blood smears are generally not favored for commercial applications.

Attempts to automate analyses of whole blood samples have met with some success, but typically have several drawbacks. For example, electrical impedance or optical flow cytometry instruments can be used to perform an LDC. Flow cytometry involves passing a diluted blood sample through a small vessel wherein electrical impedance or optical sensors can evaluate the constituent cells as they pass serially through the vessel. These instruments typically require fluid handling equipment and require the sample be diluted.

What is needed is an apparatus and method for performing automated analyses on a whole blood sample, including an LDC, which can overcome the limitations of the prior art, including the time required to perform the analysis, the operator skill level required to perform the analysis, and one that can provide greater versatility than known prior art methods and apparatus.

SUMMARY OF THE INVENTION

According to an aspect of the present invention, a method for identifying at least one type of white blood cell (WBC) within a whole blood sample is provided, comprising the steps of: a) adding at least one colorant to the whole blood sample, which colorant is operable to differentially identify at least one WBC type from another WBC type; b) disposing the blood sample into a chamber defined by at least one transparent panel; c) creating at least one image of the sample quiescently residing within the chamber; d) identifying WBCs within the sample image; e) quantitatively analyzing at least some of the identified WBCs within the image relative to one or more predetermined quantitatively determinable features; and f) identifying at least one type of WBC from the identified WBCs using the quantitatively determinable features.

According to another aspect of the present invention, an apparatus for analyzing a whole blood sample quiescently residing within a chamber is provided. The apparatus includes an objective lens, a sample illuminator, an image dissector, and a programmable analyzer. The sample illuminator is operable to provide a fluorescent excitation light and one or more transmission lights. The image dissector is adapted to receive one or both of light fluorescing from the sample and lights transmitted through the sample, and produce signals representative of such light. The programmable analyzer is adapted to receive the signals representative of the light and create at least one image of the sample quiescently residing within the chamber. The programmable analyzer is further adapted to quantitatively analyze the image to identify WBCs within the image, and to quantitatively analyze at least some of the identified WBCs within the image relative to one or more predetermined quantitatively determinable features. The programmable analyzer is operable to identify and enumerate at least one type of WBC from the identified WBCs using the quantitatively determinable features.

According to another aspect of the present invention, a method for identifying one or more target constituents within a biological sample is provided. The method includes the steps of: a) adding at least one colorant to the sample, which colorant is operable to distinguish target constituents within the sample; b) disposing the sample into a chamber defined by at least one transparent panel; c) creating at least one image of the sample quiescently residing within the chamber; d) identifying target constituents within the sample image; e) quantitatively analyzing at least some of the identified target constituents within the image relative to one or more predetermined quantitatively determinable features; and f) identifying at least one type of target constituent within the identified target constituents using the quantitatively determinable features.

These and other objects, features and advantages of the present invention will become apparent in light of the detailed description of the invention provided below, and as illustrated in the accompanying drawings.

BRIEF DESCRIPTION OF THE DRAWINGS

The application file contains at least one drawing executed in color. Copies of this patent or patent application publication with color drawing(s) will be provided by the Office upon request and payment of the necessary fee.

The principles of the invention are further clarified by referring to the following figures, where:

FIGS. 5A-5D are composite images of a lymphocyte (5A), a neutrophil (5B), an eosinophil (5C), and a monocyte (5D).

FIGS. 6A-6D are images of red light fluorescing from a lymphocyte (6A), a neutrophil (6B), an eosinophil (6C), and a monocyte (6D).

FIGS. 7A-7D are images of green light fluorescing from a lymphocyte (7A), a neutrophil (7B), an eosinophil (7C), and a monocyte (7D).

FIGS. 8A-8D are images of optical density at a blue light wavelength with cell boundary marked by red curves for a lymphocyte (8A), a neutrophil (8B), an eosinophil (8C), and a monocyte (8D).

FIGS. 9A-9D are images of Cells where contiguous pixels depicting red and green light fluorescence above a predetermined intensity are masked for a lymphocyte (9A), a neutrophil (9B), an eosinophil (9C), and a monocyte (9D).

FIGS. 10A-10D are images of Cells where contiguous pixels depicting green light fluorescence above a predetermined intensity are masked for a lymphocyte (10A), a neutrophil (10B), an eosinophil (10C), and a monocyte (10D).

FIGS. 11A-11D are images that include one or more groups of contiguous pixels depicting a regional maximum intensity in a fluorescent green channel for a lymphocyte (11A), a neutrophil (11B), an eosinophil (11C), and a monocyte (11D).

FIGS. 12A-12D are images of Cells where contiguous pixels having a blue OD value above a predetermined threshold are masked for a lymphocyte (12A), a neutrophil (12B), an eosinophil (12C), and a monocyte (12D).

FIG. 13 is a graph depicting empirical data (in the form of a probability density function—pdf) collected from a training set of sample images for each of lymphocytes, neutrophils, eosinophils, and monocytes, versus a number of Lobes. The term "probability density function" describes the likelihood that a feature has a particular value. For features with discrete values like the number of lobes, the pdf is the same as the frequency that a feature has a particular value. For example, FIG. 13 shows that around 83% of the lymphocytes within a population have just one lobe, around 15% of the lymphocytes have two lobes. Note this number of lobes is computed from the sample images and thus can have a value different from the actual biologic constituents due to image imperfection and limitation of the image analyzing algorithm. All the features computed for the images are approximations of their corresponding biological ones and some degree of inaccuracy is inherent. However, under the present invention these inherent inaccuracies can be greatly reduced by utilizing multiple features together during the analysis (e.g., an LDC), thereby resulting in an analysis having a high degree of accuracy.

FIG. 25B contains images similar to those in FIG. 25A, including encircling lines to facilitate the identification of the inner and outer parts.

FIG. 29 is a graph depicting empirical data (in the form of a pdf) collected from a training set for each of lymphocytes, neutrophils, eosinophils, and monocytes, versus the Cell Absorption Texture at 413 nm for each of the aforesaid WBCs.

FIG. 30 is a table of WBC types and features associated with the particular WBC type.

DETAILED DESCRIPTION OF THE INVENTION

Figure 1:
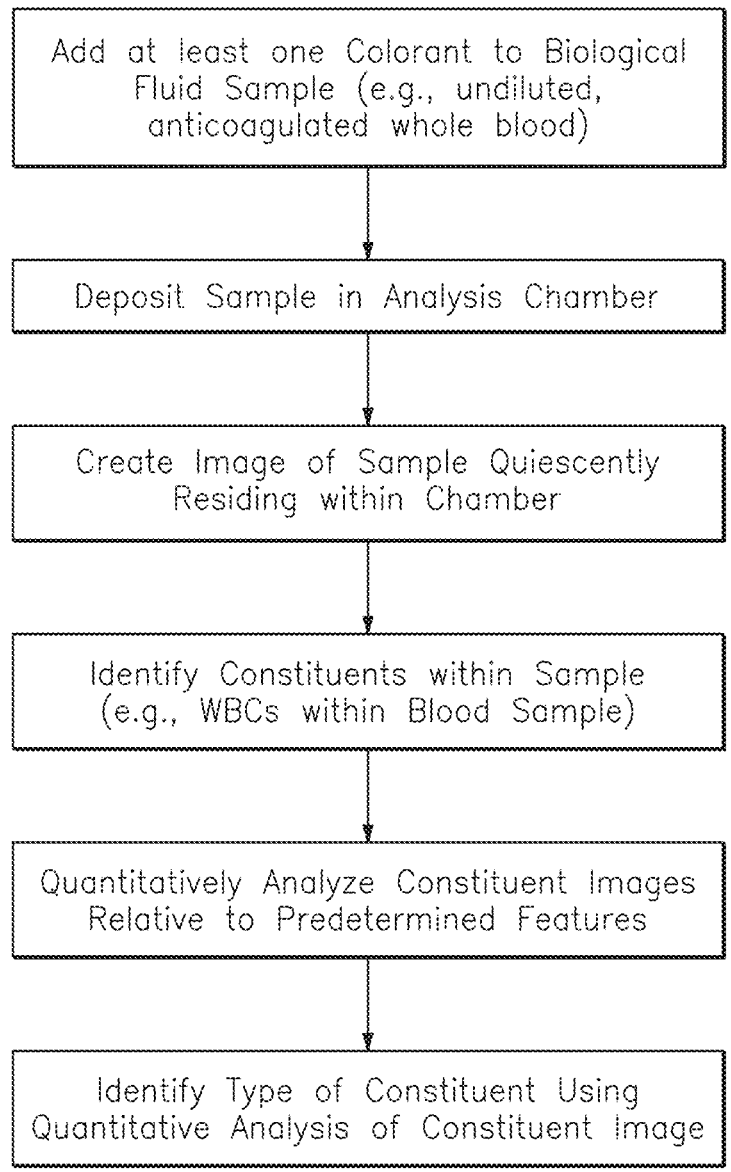
FIG. 1 is a block diagram of the present invention method.

Now referring to FIG. 1, as will be described in greater detail below, the present invention includes a method and an apparatus for identifying constituents within a biological fluid sample quiescently residing within an analysis chamber. Typically, at least one colorant is added to the fluid sample to facilitate distinguishing one constituent from another within the sample. The fluid sample quiescently residing within the chamber is imaged, and constituents within the image of the fluid sample are located. At least some of the constituents located within the image are analyzed to determine the presence of one or more features (e.g., to determine the extent to which a constituent possesses a particular characteristic) of each particular constituent analyzed. Each feature can be quantitatively evaluated from the image. At least one type of constituent is determined from the located constituents using the features.

The present invention has particular utility when applied to perform a leukocyte differential count ("LDC") on a whole blood sample. As indicated above, an LDC is an analysis wherein the different types of WBCs are identified and enumerated. The results can be expressed in terms of the relative percentages of the identified WBC types. The present invention can be used to distinguish, amongst other things, constituents (e.g., WBCs) such as monocytes, eosinophils, neutrophils, and lymphocytes within a blood sample. To illustrate the utility of the present invention, the invention will be described in terms of an LDC application for identifying monocytes, eosinophils, neutrophils, and lymphocytes. The present invention is not limited to this particular application, however, and can be used to identify other types of constituents within a whole blood sample, or constituents within other types of biological samples utilizing constituent features that are quantitatively determinable from one another from an image of the sample.

As indicated above, the present invention is operable to perform an analysis on a fluid sample of whole blood quiescently residing within a chamber, which chamber includes at least one transparent panel. The present invention is not limited to use with any particular chamber embodiment. Examples of acceptable chambers are described in U.S. Patent Application Publication No. 2007/0243117 and U.S. Patent Provisional Application No. 61/287,955 (referred to hereinafter as the "'955 Application"), each of which applications is hereby incorporated by reference in its entirety. As indicated in the '955 Application, the chamber is typically sized to hold about 0.2 to 1.0 µl of fluid sample, but the chamber is not limited to any particular volume capacity, and the capacity can vary to suit the analysis application. The chamber is operable to quiescently hold a liquid sample. The term "quiescent" is used to describe that the fluid sample is deposited within the chamber for analysis, and is not purposefully moved during the analysis. To the extent that motion is present within the fluid blood sample, it will predominantly be due to Brownian motion of the blood sample's formed constituents.

Figure 2:
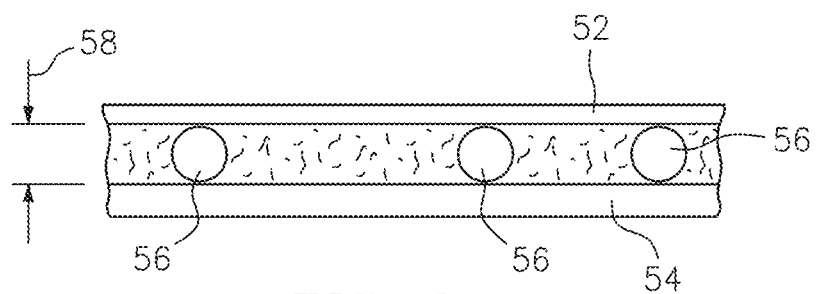
FIG. 2 is a diagrammatic section view of a chamber.
Figure 3:
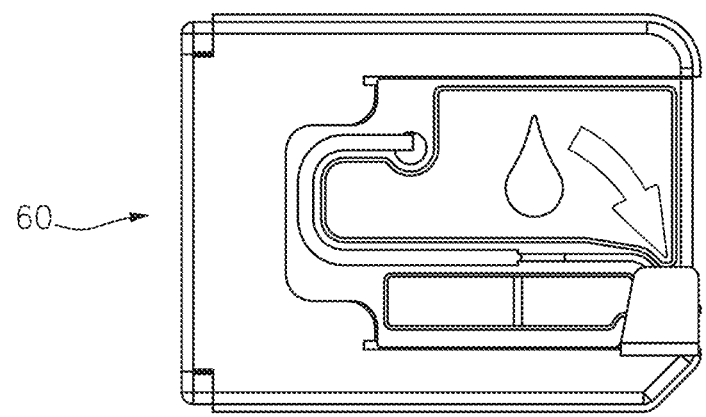
FIG. 3 is a diagrammatic top view of a biologic fluid sample cartridge, of the type that can include a chamber such as that shown in FIG. 2.

An example of an acceptable chamber type is shown in FIGS. 2 and 3. The chamber 50 is formed by a first planar member 52, a second planar member 54, and at least three separators 56 disposed between the planar members 52,54. At least one of the planar members 52,54 is transparent. The separators 56, which separate the planar members 52,54 to form the chamber 50, help to establish the height 58 of the chamber 50. At least one of the planar members 52,54 or the separators 56 is sufficiently flexible to permit the mean chamber height 58 between the members to closely approximate the mean height of the separators 56.

The above described chamber 50 can be implemented in a variety of different embodiments. The '955 Application" describes an embodiment wherein the chamber 50 is disposed within a sample collection and analysis cartridge 60 (see FIG. 3). The cartridge 60 is adapted for use with an automated analysis device 62 (shown diagrammatically in FIG. 4) having imaging hardware and a processor (e.g., programmable analyzer) for controlling, processing, and analyzing images of the sample.

Figure 4:
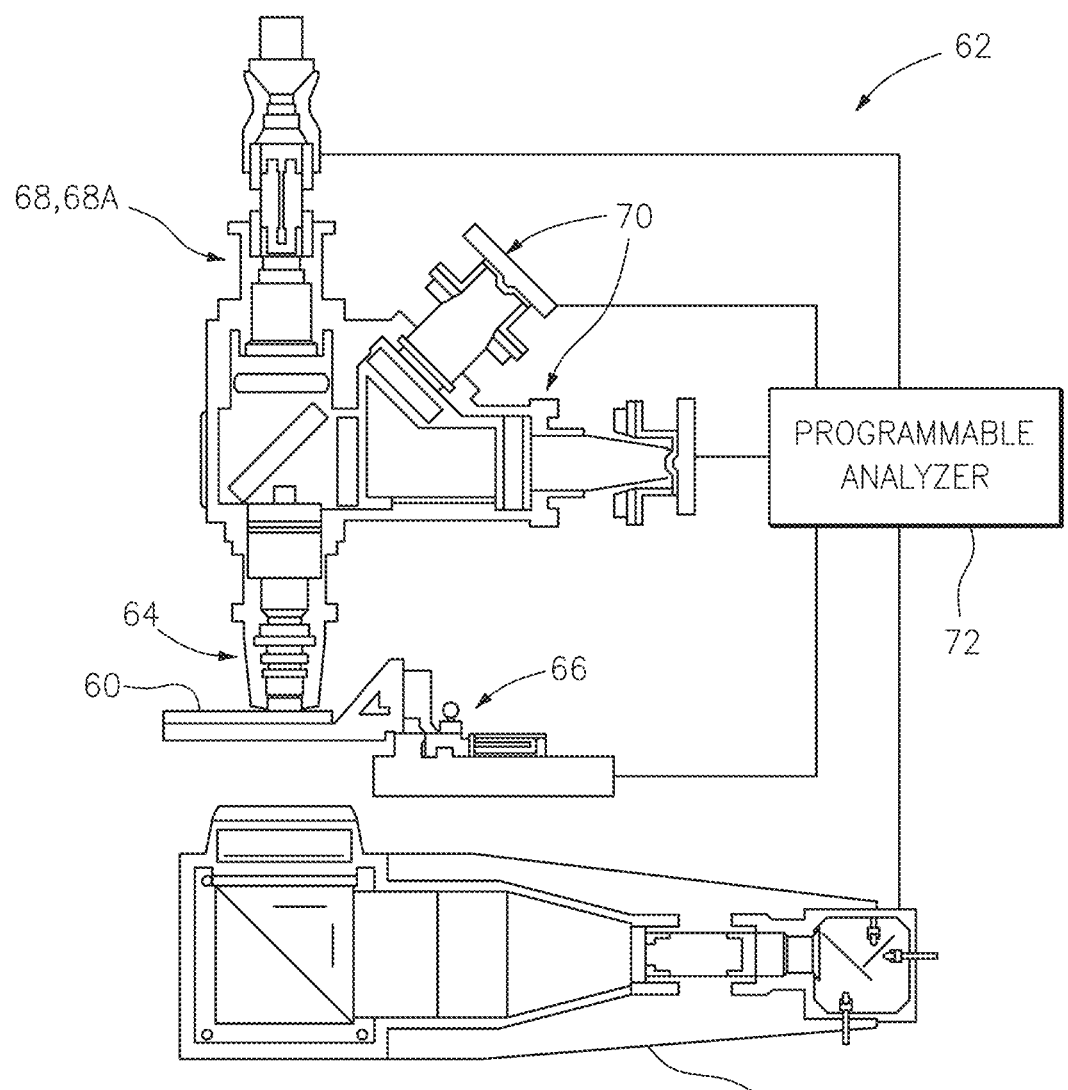
FIG. 4 is a diagrammatic view of an analysis device operable to perform an analysis on a sample disposed within a chamber.

Referring to FIG. 4, an analysis device 62 operable to be used with the above described chamber typically includes an objective lens 64, a cartridge holding and manipulating device (e.g., a motorized stage) 66, a sample illuminator 68, an image dissector 70, and a programmable analyzer 72. One or both of the objective lens 64 and cartridge holding device 66 are movable toward and away from each other to change a relative focal position of the device relative to the chamber and the sample disposed therein.

The sample illuminator 68 illuminates the sample using light along predetermined wavelengths. For example, the sample illuminator can include an epi-fluorescence light source 68A and a transmission light source 68B. As will be explained below, colorants such as Acridine Orange (also referred to as "Basic Orange 15" or "ACO") and Astrazon Orange (also referred to as "AO" or Basic Orange 21) emit light at particular wavelengths when mixed with whole blood and subjected to an excitation wavelength from the epi-fluorescent light source, which source typically produces light within the range of about 450-490 nm. An excitation wavelength at about 470 nm is particularly useful. The transmission light source is operable to produce light at wavelengths associated with one or more of red, green, and blue light. The red light is typically produced in the range of about 600-700 nm, with red light at about 660 nm preferred. The green light is typically produced in the range of about 515-570 nm, with green light at about 540 nm preferred. As will be discussed below, the blue light is typically in the range of about 405-425 nm, with blue light at about 413 nm preferred. Light transmitted through the sample, or fluoresced from the sample, is captured using the image dissector, and a signal representative of the captured light is sent to the programmable analyzer, where it is processed into an image. The image is produced in a manner that permits the light transmittance or fluorescence intensity captured within the image to be determined on a per unit basis; e.g., "per unit basis" being an incremental unit of which the image of the sample can be dissected, such as a pixel.

An example of an acceptable image dissector 70 is a charge couple device (CCD) type image sensor that converts light passing through (or from) the sample into an electronic data format image. Complimentary metal oxide semiconductors ("CMOS") type image sensors are another example of an image sensor that can be used. The signals from the image dissector provide information for each pixel of the image, which information includes, or can be derived to include, intensity, wavelength, and optical density. Intensity values are assigned an arbitrary scale of, for example, 0 units to 4095 units ("IVUs"). Optical density ("OD") is a measure of the amount of light absorbed relative to the amount of light transmitted through a medium; e.g., the higher the "OD" value, the greater the amount of light absorbed during transmission. OD can be quantitatively described in optical density units ("OD") or fractions thereof; e.g., a MilliOD is a $\frac{1}{1000}^{th}$ of an OD. One "OD" unit decreases light intensity by 90%. "OD" or "MilliOD" as a quantitative value can be used for images acquired or derived by transmission light, for example, the transmission blue light illustrates in FIGS. 8A-8D. The information from the image dissector is separated into multiple channels. The information from the image dissector will be described hereinafter as being separated into three channels, which number provides particular utility for determining a four part LDC. The present invention is not limited to a three channel embodiment, however. A first of the three channels is directed toward information relating to light emitted from the sample at a first wavelength (e.g., 540 nm, which appears green). A second channel is directed toward information relating to light emitted from the sample at a second wavelength (e.g., 660 nm, which appears red). A third channel is directed toward information relating to light passing through the sample at a third wavelength (e.g., 413 nm, which is used to determine blue optical density—"OD"). These wavelength values and the number of channels have particular utility when an LDC is being performed on a whole blood sample. The present invention is not limited to these particular wavelengths or number of channels. Additional channels can be implemented to gather information at different wavelengths and/or transmission values. That information, in turn, can be used to evaluate additional constituents within the sample and/or to increase the accuracy of the analysis. For example, in applications where it is desirable to further differentiate basophils within the sample, a fourth and a fifth channel can be added. The fourth channel can be directed toward information relating to light passing through the sample at a fourth wavelength (e.g., 540 nm), which is used to determine green OD, and the fifth channel can be directed toward information relating to light passing through the sample at a fifth wavelength (e.g., 660 nm), which is used to determine red OD. These OD values, in turn, can be used to identify basophils.

The programmable analyzer includes a central processing unit (CPU) and is in communication with the cartridge holding and manipulating device, sample illuminator and image dissector. The programmable analyzer is adapted (e.g., programmed) to send and receive signals from one or more of the cartridge holding and manipulating device, the sample illuminator, and an image dissector. For example, the analyzer is adapted to: 1) send and receive signals from the cartridge holding and manipulating device to position the cartridge and chamber relative to one or more of the optics, illuminator, and image dissector; 2) send signals to the sample illuminator to produce light at defined wavelengths (or alternatively at multiple wavelengths); and 3) send and receive signals from the image dissector to capture light for defined periods of time. It should be noted that the functionality of the programmable analyzer may be implemented using hardware, software, firmware, or a combination thereof. A person skilled in the art would be able to program the processing unit to perform the functionality described herein without undue experimentation.

The programmable analyzer is further adapted to process the signals received from the image dissector according to one or more predetermined algorithms. The specifics of a particular algorithm will depend upon the analysis at hand. As indicated above, the present invention has particular utility when applied to perform an LDC on a whole blood sample, and to illustrate that utility the invention is described herein as performing an LDC. The present invention is not limited to this particular analysis, however.

To perform the LDC, the algorithm utilizes a set of identifying features, each of which features is distinguishable from the other features and each of which is quantitatively determinable from an image of the sample. Each WBC can be characterized by the presence or absence of certain identifying features, and/or by quantitative information associated with certain features. For purposes of providing an enabling disclosure, the present invention is described herein in terms of an exemplary set of identifying features that can be used to selectively identify and distinguish WBCs. This set is not inclusive of all possible features, and therefore the present invention is not limited to this particular set.

For a WBC analysis, an exemplary set of identifying features includes those entitled: Cell, Nucleus, number of Lobes, Cell Area, Nucleus Area, Ratio of Large Granules, Ratio of Nucleus, Red-Green Ratio, Nucleus Shape, Cell Shape, Nucleus Brightness, Cytoplasm Brightness, Average Cell Absorption at a Given Wavelength, Nucleus Texture, Cytoplasm Texture, Cell Absorption Texture at a Given Wavelength, Nucleus Hollowness, and Cytoplasm Hollowness; each of which is described below.

In some instances, certain features directly provide information about a particular cell (e.g., Nucleus Shape). In other instances, a feature (e.g., Cell Area) can be used to indirectly provide information about a particular cell (e.g., ratio of Nucleus Area to Cell Area—referred to above as "Ratio of Nucleus", etc.).

The identifying features are based on quantifiable characteristics such as light intensity, light color, OD, area, and relative position (e.g., shape). As indicated above, the colors are created by one or more colorants admixed with the sample, which upon excitation, produce fluorescent light emission at particular wavelengths associated with particular colors. An example of an acceptable colorant that can be used when performing an LDC on a whole blood sample is Acridine Orange ("ACO"). ACO is a fluorescent dye that, when mixed with a whole blood sample, selectively stains constituents within the sample; e.g., white blood cells, platelets, reticulocytes, and nucleated red blood cells. With respect to WBCs, the ACO permeates through the respective WBC and stains its DNA and RNA. The color(s) emitted by the dye within the WBC are a function of a number of factors, including: the quantity of RNA and DNA within the dye, the concentration of the dye in the constituent, and the pH of the constituent. The present invention is not limited to using ACO, and other dyes (e.g., Astrazon Orange) may be used in place of ACO or in combination with ACO. Using ACO and white blood cells as an example, if the sample is subjected to an excitation light at or about a wavelength of 470 nm, the ACO bound to materials (e.g., DNA) within the nucleus of a white blood cell will emit light at about 540 nm (which appears green), and the ACO bound to materials (e.g., RNA) within the cytoplasm of a white blood cell will emit light at about 660 nm (which appears red).

As indicated above, OD values within the sample are a function of absorptivity of light at predetermined wavelengths by materials that naturally occur within the cell (e.g., hemoglobin), and/or may be a function of colorant absorbed (or not absorbed) by constituents within the sample.

The identification of particular groups of pixels at one or more defined wavelengths can be performed using a variety of different techniques. For example, segmentation techniques can be used to produce a masked image depicting only those pixels within the image that meet the criteria (e.g., intensity and color). For those analyses that derive information only from the green light portions (e.g., the nuclei) or the red light portions (e.g., cytoplasm) of the image, or both, the sample image can be masked to produce a partial image depicting only those pixels showing green, or red, or both, and may also be distinguished by a predetermined intensity threshold. The present invention is not limited to any particular segmentation technique, and a specific technique can be chosen in view of the application at hand. For example, a hard segmentation technique can be used wherein a pixel is assigned as either belonging to an object or not. "Hard" segmentation techniques can be implemented using thresholding, region grow, or watershed type routines. Alternatively, soft segmentation techniques can be utilized; e.g., a "fuzzy" segmentation, where each pixel is assigned a value in the range of 0 to 1, which value describes the likelihood that the particular pixel belongs to the object. The description of each of the identifying features below will provide clear examples of how quantitative data such as that associated with wavelength and intensity can provide a basis for distinguishing one WBC from another. The present invention is also not limited to using a segmentation technique, and can use other techniques that select (i.e., "pick") pixels or otherwise distinguish pixels having particular attributes.

The term "Cell" refers to an identifying feature that includes a group of substantially contiguous pixels within the image depicting green light emission and/or red light emission at a high level of intensity (i.e., at or above a predetermined IVU threshold) relative to the intensity of the entire image. Hence, those pixels that have the predetermined color (e.g., red and green) at or above a predefined intensity level are identified quantitatively. FIGS. 5A-5D, for example, illustrate a region containing WBCs within the specimen image showing green light and red light. FIGS. 9A-9D illustrate a region at or above the threshold intensity level; i.e., a group of substantially contiguous pixels within the above images that define a cell, The term "Nucleus" refers to an identifying feature that includes a group of contiguous pixels within the image depicting green light emission at a high intensity level relative to the intensity level of the entire image. As indicated above, segmentation techniques can be used to produce a masked image depicting only those pixels within the image that meet the quantitative value criteria of green emission at or above the predetermined intensity threshold value. Each group of contiguous pixels within the image depicting green light emission at or above the IVU threshold is thereby characterized as a "Nucleus" feature. As indicated above, FIGS. 10A-10D illustrate a masked image showing a Nucleus feature.

The term "Lobe" refers to an identifying feature that includes a group of contiguous pixels within the image that are a regional maximum intensity in the fluorescent green channel (e.g., 540 nm). The term "regional maximum intensity" refers to a group of pixels having substantially the same intensity value (i.e., a quantifiable value), which value is noticeably greater than surrounding pixels. FIG. 11A illustrates a WBC having a single lobe, identifiable by the single group of pixels exhibiting regional maximum emission intensity. FIGS. 11C and 11D illustrate a WBC having a pair of lobes. FIG. 11B illustrates a WBC having three lobes. FIG. 13 graphically illustrates the differences in number of Lobes (i.e., a quantifiable value) associated with lymphocytes, neutrophils, monocytes, and eosinophils. The number of Lobes associated with neutrophils, for example, makes number of Lobes an identifying feature that can be used to distinguish neutrophils.

FIGS. 13, 14, 16-18, 21-24, and 26-29 are graphs depicting empirical data gathered from training sets of WBC images. The graphs include a vertical axis with probability density function ("pdf") values versus a horizontal axis with relevant quantifiable data for the particular identifying feature. These graphs illustrate well the relationship between WBCs and the respective feature, but the present invention is not limited to these particular types of graphs. For example, probability density functions are a statistical representation of the empirical data from the training sets. Other statistical representations may be used alternatively.

Figure 14:
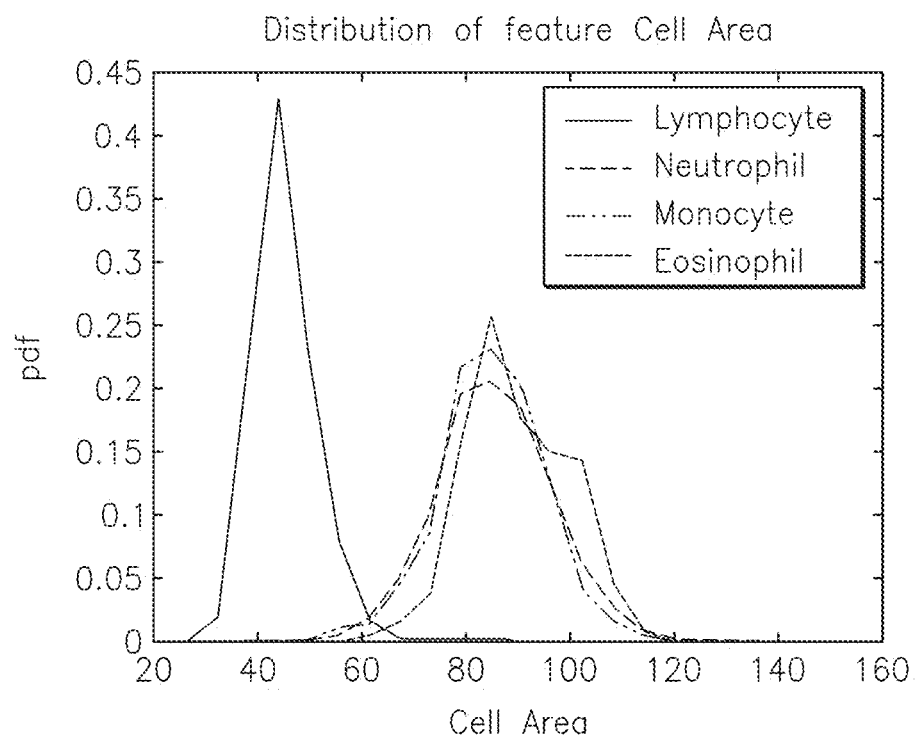
FIG. 14 is a graph depicting empirical data (in the form of a probability density function—pdf) collected from a training set for each of lymphocytes, neutrophils, eosinophils, and monocytes, versus the determined Cell Area for each of the aforesaid WBCs.

"Cell Area" is an identifying feature that refers to the quantifiable area within the image that is identified as a particular Cell. Because each pixel represents a known area of the image, the area of a given cell or other constituent or element can be determined from the number of pixels. The present invention is not limited, however, to this method of determining a Cell Area value. FIG. 14 graphically illustrates the differences in Cell Area associated with lymphocytes, neutrophils, monocytes, and eosinophils. The Cell Area associated with lymphocytes, for example, makes Cell Area an identifying feature that can be used to distinguish lymphocytes.

"Nucleus Area" is an identifying feature that refers to the area within the image that is identified as a particular Nucleus. The Nucleus Area can, for example, be determined in the manner described above for determining the Cell Area. The numerical value of the determined Nucleus Area provides the quantifiable value of the Nucleus Area.

Figure 15:
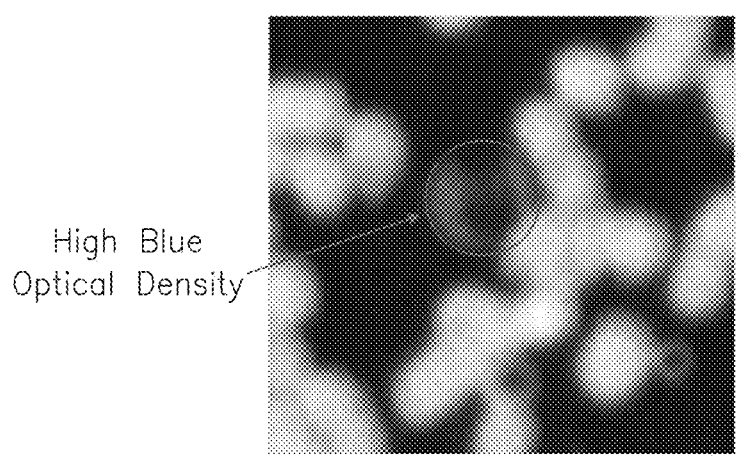
FIG. 15 is an image depicting the high blue OD areas within a Cell.
Figure 16:
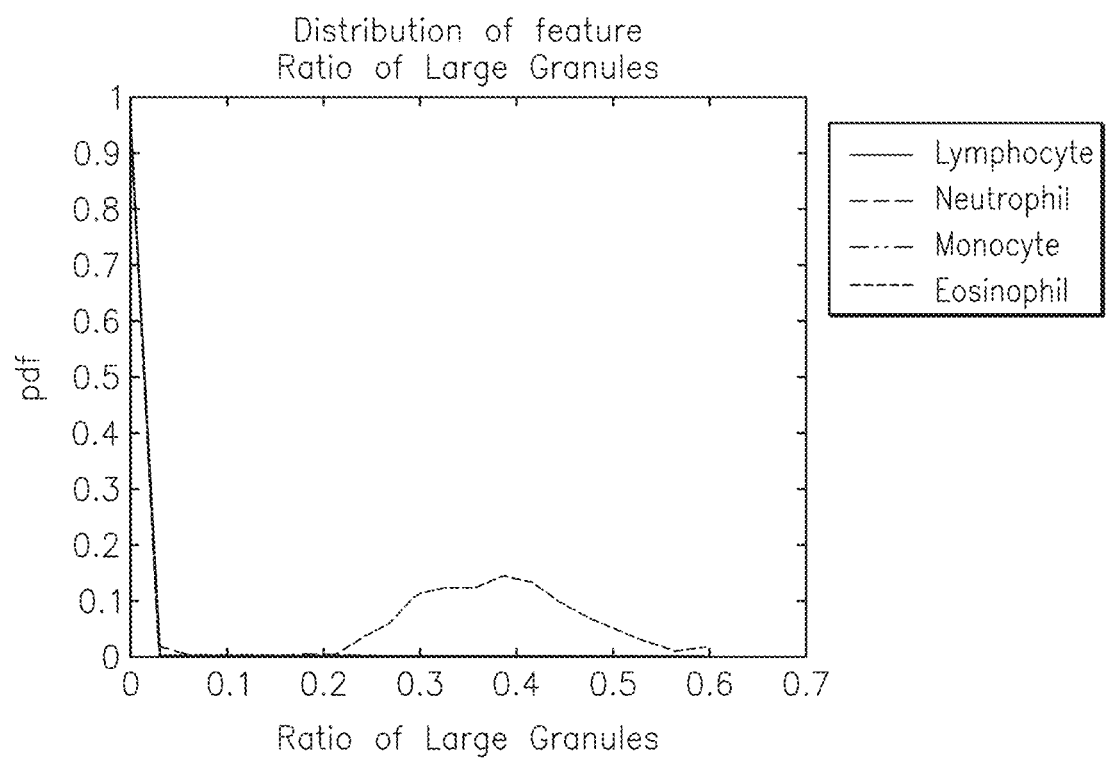
FIG. 16 is a graph depicting empirical data (in the form of a pdf) collected from a training set for each of lymphocytes, neutrophils, eosinophils, and monocytes, versus the Ratio of Large Granules for each of the aforesaid WBCs.

"Ratio of Large Granules" is an identifying feature that is a ratio of the sum of high blue OD areas within a Cell, over the Cell Area. The term "high blue OD area"—also referred to as a "Large Granule"—refers to a group of contiguous pixels within the image that have a blue OD value that is above a predetermined threshold (i.e., a quantifiable value). The blue OD value is created by transmitting blue light at a wavelength of about 413 nm through the sample. The transmitted blue light that is used to determine the blue OD value, can be in the range of about 405-425 nm. Transmitted blue light at about 413 nm is advantageous because hemoglobin (HGB) has its peak absorption at or about 413 nm. Each Large Granule appears as a group of bright pixels within the OD image and each can be detected by segmentation techniques within an OD image, masking all pixels except those that have an OD above a predetermined threshold (e.g., >300 milliOD). FIG. 15 illustrates an example of high blue OD areas within a Cell (i.e., large granules within an eosinophil). FIGS. 12A-12D further illustrate the pixels with high blue OD in different types of WBCs. Our research to date indicates that relative to the Cells considered within the LDC, only eosinophils have significant regions of the high intensity blue OD within the Cell. FIG. 16 graphically illustrates the differences in the Ratio of Large Granules associated with lymphocytes, neutrophils, monocytes, and eosinophils. As can be seen from FIG. 16, the Ratio of Large Granules is a quantifiable identifying feature that can be used to readily distinguish eosinophils from the other constituents within the LDC.

Figure 17:
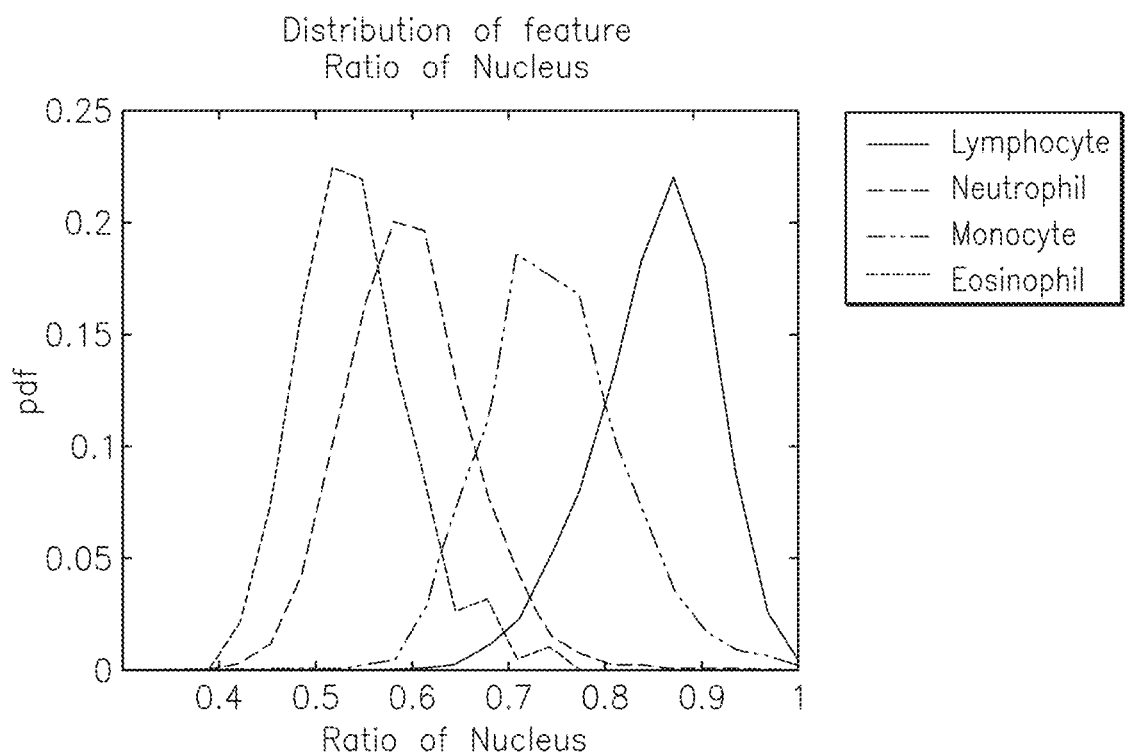
FIG. 17 is a graph depicting empirical data (in the form of a pdf) collected from a training set for each of lymphocytes, neutrophils, eosinophils, and monocytes, versus the Ratio of Nucleus for each of the aforesaid WBCs.

"Ratio of Nucleus" is an identifying feature that is a ratio of a Nucleus Area over the Cell Area, as those features are defined above. FIG. 17 graphically illustrates the differences in the Ratio of Nucleus (i.e., the quantifiable value) associated with lymphocytes, neutrophils, monocytes, and eosinophils. The Ratio of Nucleus associated with lymphocytes, for example, makes Ratio of Nucleus an identifying feature that can be used to distinguish lymphocytes.

Figure 18:
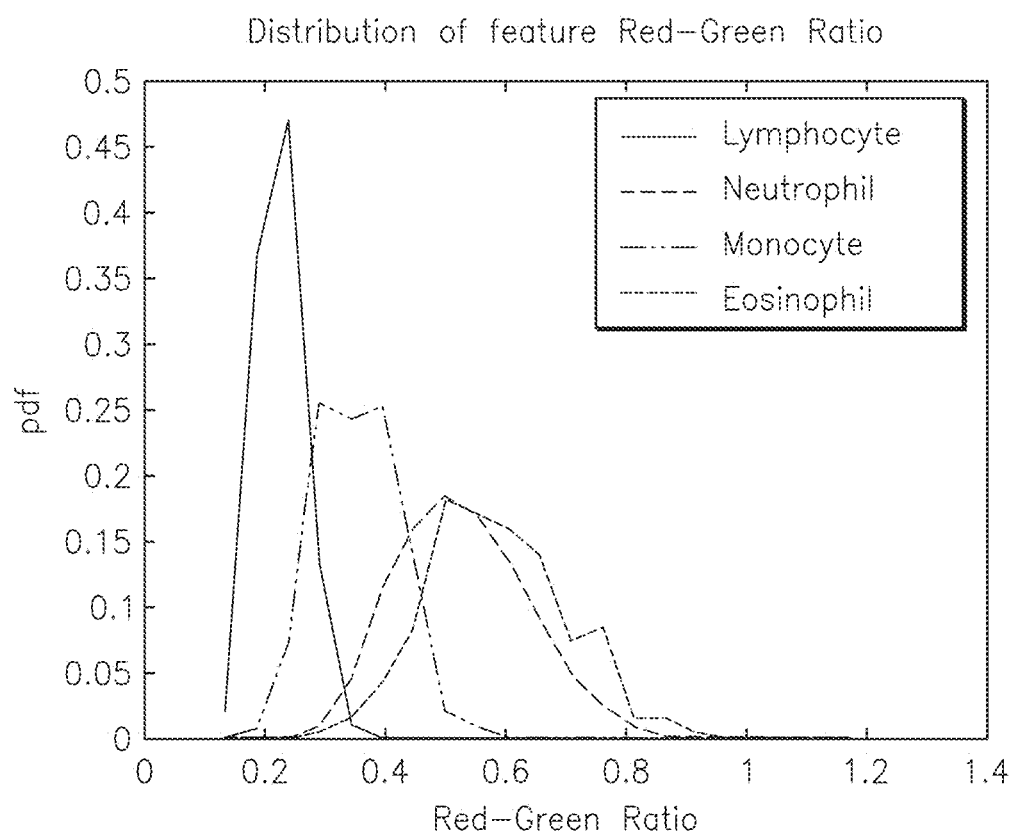
FIG. 18 is a graph depicting empirical data (in the form of a pdf) collected from a training set for each of lymphocytes, neutrophils, eosinophils, and monocytes, versus the Red-Green Ratio for each of the aforesaid WBCs.

"Red-Green Ratio" is an identifying feature that is a ratio of the mean intensity value of those pixels (or area) within an identified Cell depicting fluorescent red light, over the mean intensity value of those pixels (or area) within the identified Cell depicting fluorescent green light (i.e., the mean values of the respective light are quantifiable values). FIGS. 6A and 7A (or 6B and 7B, or 6C and 7C, or 6D and 7D) illustrate the combined fluorescent red and fluorescent green of a particular type of Cell. The image shown in FIG. 6A (or 6B, 6C, or 6D) is a partial image depicting only the component from the fluorescent red light, and the image shown in FIG. 7A (or 7B, 7C, or 7D) is a partial image of the same Cell depicting only the component from the fluorescent green light. The Red-Green Ratio is the ratio of the mean intensity values of the respective colors. FIG. 18 graphically illustrates the differences in the Red-Green Ratio associated with lymphocytes, neutrophils, monocytes, and eosinophils. The Red-Green Ratio associated with lymphocytes, for example, makes Red-Green Ratio an identifying feature that can be used to distinguish lymphocytes.

Figure 19:
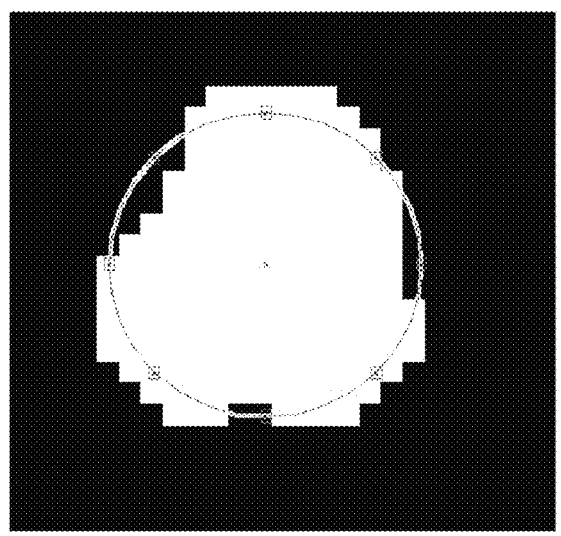
FIG. 19 is an image depicting the pixels associated with the Nucleus of a Cell masked out, with a circle applied to the image to approximate the masked area.
Figure 20:
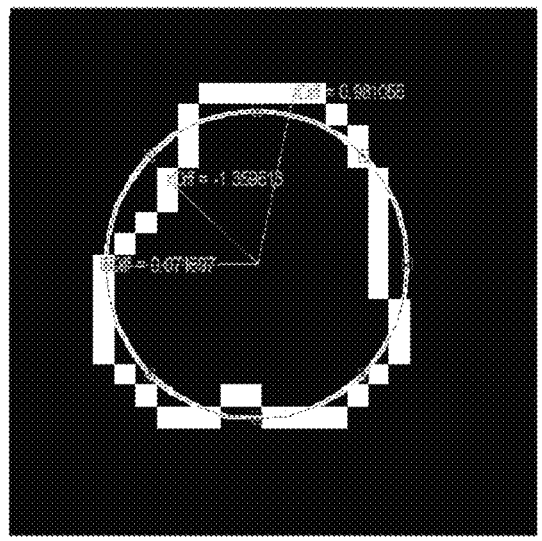
FIG. 20 is a version of the image shown in FIG. 19, highlighting only those pixels at the boundary of the masked area (i.e., at the boundary of the Nucleus), including a centroid and a few illustrative positioning line segments extending between the centroid and the relevant boundary pixel.

"Nucleus Shape" is an identifying feature that describes the circularity of a Nucleus. A variety of geometric techniques can be used to determine the circularity of a nucleus within the specimen image, which nucleus appears as a two-dimensional body within the image. For example, in terms of a single Cell, a segmentation technique can be used to identify those pixels that are associated with the nucleus of the Cell (i.e., those pixels that show green). Once the Nucleus pixels are identified, the pixels located at the boundary of the Nucleus are identified. The centroid of the Nucleus (i.e., the centroid of the area covered by the Nucleus) can be defined by averaging the position of all of the boundary pixels. A circle that approximates the pixel defined body, and which is centered on the centroid, is applied to the pixel body. FIG. 19 illustrates an example of a nucleus defined by pixels within a masked image, and a circle applied to the pixel body. FIG. 20 illustrates the corresponding boundary pixels. The locations of the boundary pixels are collectively used to determine the circularity of the Nucleus; e.g., the deviation value of the boundary pixels from the approximating circle (i.e., a quantifiable value). For example, the location of each boundary pixel can be described in normalized terms by dividing the difference of the radius of the boundary pixel ($r_{BP}$) less the radius of the circle ($r_c$), by the radius of the circle:

$$rNormalized = \frac{rDiff}{r_c} = \frac{r_{BP} - r_c}{r_c}$$

Figure 21:
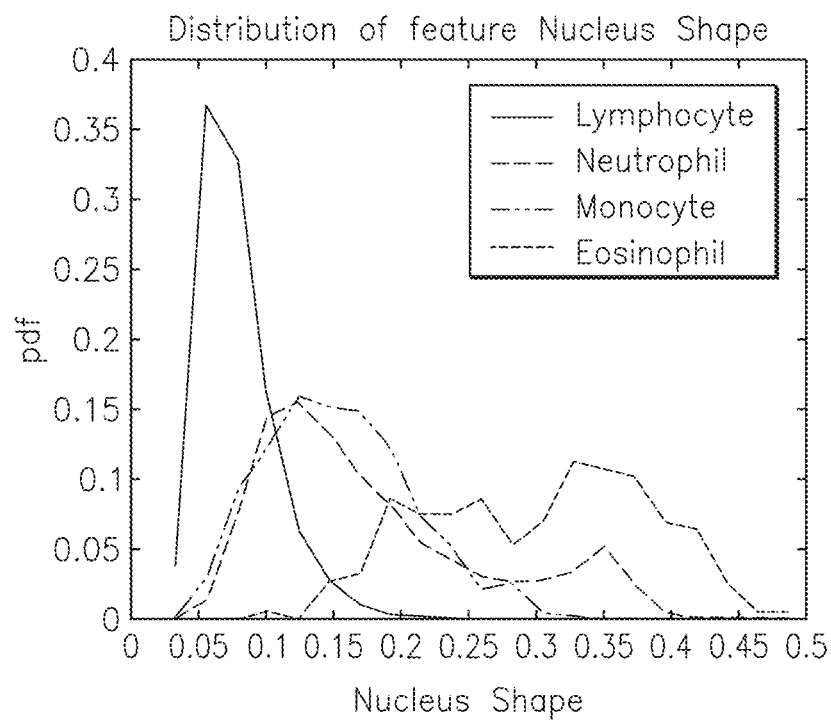
FIG. 21 is a graph depicting empirical data (in the form of a pdf) collected from a training set for each of lymphocytes, neutrophils, eosinophils, and monocytes, versus the Nucleus Shape for each of the aforesaid WBCs.

If the boundary pixel is located on the circle, the numerator ($r_{BP}-r_c$) equals zero and the deviation is zero. The deviation (rNormalized) from the circularity can then be used as a measure of the circularity of the shape; e.g., the circularity of the Nucleus. FIG. 21 depicts a graph comparing the circularity of the Nucleus for a statistically significant population of lymphocytes, neutrophils, monocytes, and eosinophils. The graph clearly shows that the circularity of the Nuclei within lymphocytes is noticeably different from the circularity of the neutrophils, monocytes, and eosinophils, thereby making Nucleus Shape an identifying feature that can be used to distinguish lymphocytes. The above described technique for determining the circularity of the Nucleus is an example of an acceptable technique and provided for enablement purposes, and the present invention is not limited to this particular technique.

Figure 22:
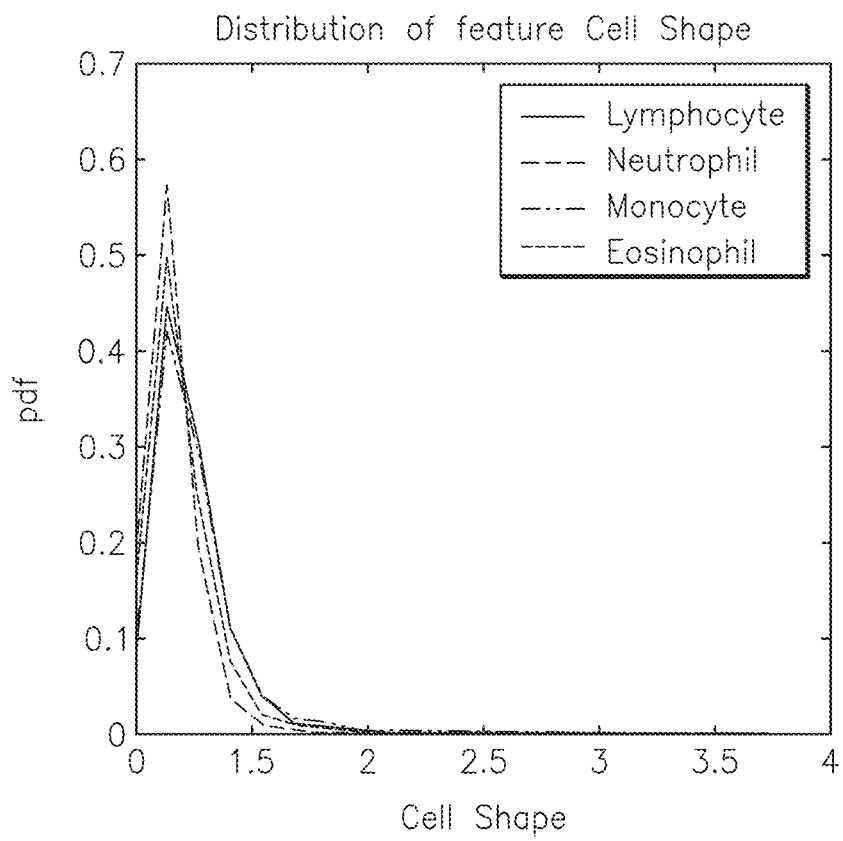
FIG. 22 is a graph depicting empirical data (in the form of a pdf) collected from a training set for each of lymphocytes, neutrophils, eosinophils, and monocytes, versus the Cell Shape for each of the aforesaid WBCs.

"Cell Shape" is an identifying feature that evaluates the shape of the boundary of a Cell; i.e., the distribution of the boundary pixels of a cell within the 2-D plane of the image. The techniques described above for determining the circularity of the Nucleus can be used to determine the Cell Shape (e.g., ellipse, oval, etc.) of the Cell. With respect to the Cell Shape, the techniques are preferably used to determine the deviation of a Cell from a shape (i.e., a quantifiable value) such as an ellipse that is a closer approximation of a naturally occurring Cell Shape. The present invention is not limited to the above described techniques, or to using an elliptical shape as an approximation. FIG. 22 graphically illustrates the differences in Cell Shape associated with lymphocytes neutrophils, monocytes, and eosinophils. The Cell Shape associated with neutrophils, for example, makes Cell Shape an identifying feature that can be used to distinguish neutrophils.

"Nucleus Brightness" is an identifying feature that quantifies the mean fluorescent green intensity values within a Nucleus. FIGS. 7A-7C show that the Nucleus of a lymphocyte, neutrophil, and eosinophil have a greater intensity (i.e., appear brighter) than the Nucleus of a monocyte (FIG. 7D). The aforesaid difference in intensity is due to the relative dense distribution of chromatin inside the lymphocyte, neutrophil, and eosinophil Nuclei, versus the sparse distribution of chromatin inside the monocyte Nucleus. In some embodiments of the present invention, the Nucleus Brightness is determined relative to a normalized value of the mean fluorescent green intensity values within a Nucleus. The normalized value helps to account for variabilities within the sample; e.g., non-uniform staining within the sample. The exact technique used to normalize the intensity values can vary to suit the application at hand, and the present invention is not limited to any particular normalization technique. For example, in some instances the intensity values of mean fluorescent green intensity values within a Nucleus can be normalized relative to intensity values of neighboring Cells, or relative to Cells throughout the sample.

"Cytoplasm Brightness" is an identifying feature that quantifies the mean fluorescent red intensity values within cytoplasm. FIGS. 6A-6D show the intensity of the fluorescent red emission from the cytoplasm region of certain Cells. The intensity of red light emitted from the cytoplasm of a lymphocyte is low relative to the intensity of red light emitted from cytoplasm of a monocyte. The intensity of red light emitted from the cytoplasm of a monocyte is, in turn, low relative to the intensity of red light emitted from cytoplasm of neutrophils and eosinophils. As indicated above, in some embodiments of the present invention brightness values are determined relative to a normalized value; e.g., a normalized mean fluorescent red intensity value within a Cell. The exact technique used to normalize the intensity values can vary to suit the application at hand, and the present invention is not limited to any particular normalization technique.

"Average Cell Absorption at A Given Wavelength" is an identifying feature that quantifies the average OD of a Cell associated with blue light at a given wavelength (e.g., the "mean blue OD intensity") transmitted through the Cell. As indicated above, the transmitted blue light can be in the range of about 405-425 nm, and transmitted blue light at about 413 nm is advantageous because at or about 413 nm is where hemoglobin has peak absorption. To quantify the mean blue OD intensity of a Cell, blue light at a wavelength of about 413 nm is transmitted through the respective Cell.

Figure 23:
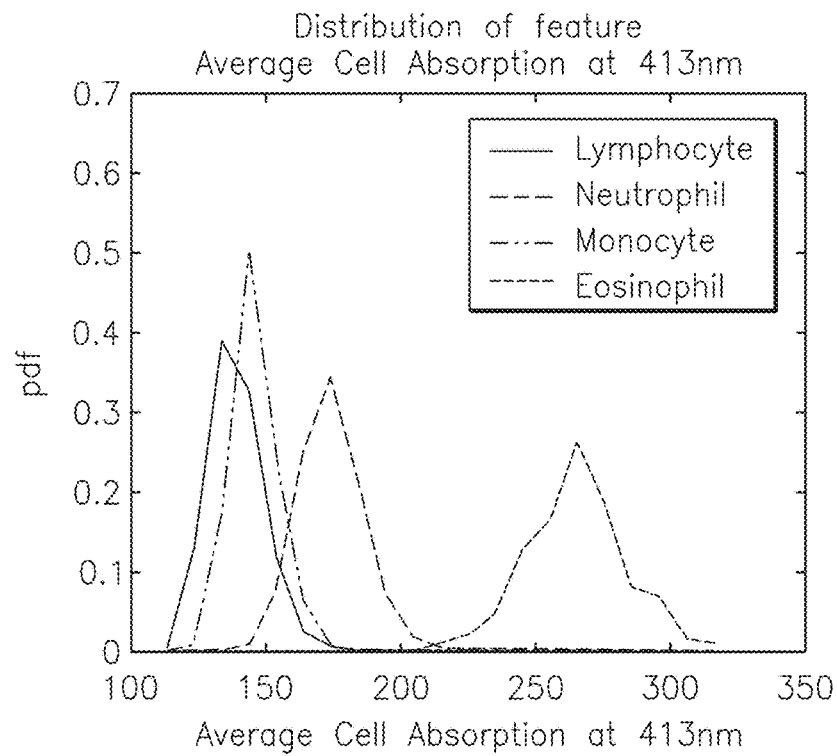
FIG. 23 is a graph depicting empirical data (in the form of a pdf) collected from a training set for each of lymphocytes, neutrophils, eosinophils, and monocytes, versus the Average Cell Absorption at 413 nm for each of the aforesaid WBCs.

The OD associated with the blue light is determined on a per pixel basis. FIGS. 9A-9D each depict masked versions of the respective Cells, where everything is masked except those pixels having fluorescent red or green intensity values greater than a predetermined threshold. The mean value of the OD (i.e., the OD associated with the 413 nm wavelength) within the masked portion of the respective Cell is determined. FIGS. 8A-8D show images of blue OD resulting from the aforesaid light being transmitted through the respective Cell. To facilitate the evaluation of FIGS. 8A-8D, an encircling line is drawn in each image indicating a boundary between the outer region and the inner region where the average cell absorption is determined. FIG. 23 graphically illustrates the differences in the Average Cell Absorption at 413 nm associated with lymphocytes, neutrophils, monocytes, and eosinophils. The Average Cell Absorption at 413 nm associated with eosinophils, for example, makes Average Cell Absorption at 413 nm an identifying feature that can be used to distinguish eosinophils, which is also evident from FIGS. 8A-8D.

Figure 24:
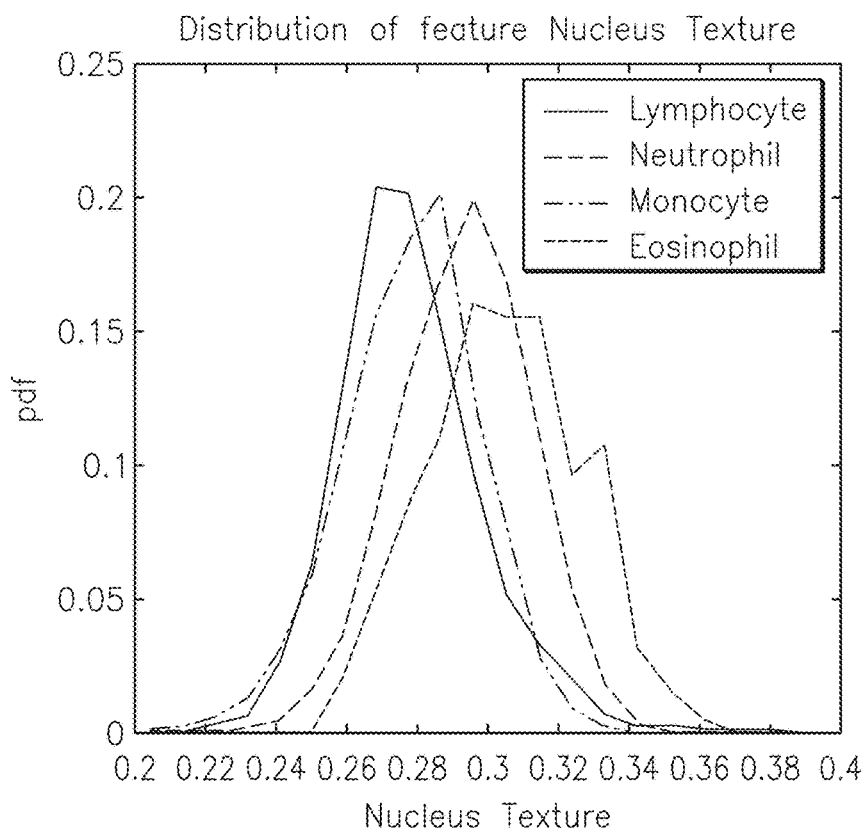
FIG. 24 is a graph depicting empirical data (in the form of a pdf) collected from a training set for each of lymphocytes, neutrophils, eosinophils, and monocytes, versus the Nucleus Texture for each of the aforesaid WBCs.

"Nucleus Texture" is an identifying feature that quantifies the "texture" of the fluorescent green light emitted within the Nucleus region of a Cell. The term "texture" is used to refer to the variability of the fluorescent green light within the Nucleus of a Cell, typically on a per pixel basis. Several different techniques can be used to quantify the Nucleus Texture. For example, the standard deviation of the mean normalized green intensity values per pixel can be used to quantify the Nucleus Texture. Normalized fluorescent green intensity values can be determined by identifying all of the pixels within a Cell that emit fluorescent green light, and assigning an arbitrary value of zero to the pixels with the lowest intensity and a value of one to the pixels of the highest intensity. The standard deviation of the intensity values (i.e., a quantifiable value) can be computed from those values using known techniques. FIG. 24 graphically illustrates the differences in the Nucleus Texture associated with lymphocytes, neutrophils, monocytes, and eosinophils. The Nucleus Texture associated with lymphocytes, for example, make Nucleus Texture an identifying feature that can be used to distinguish lymphocytes.

Figure 25A:
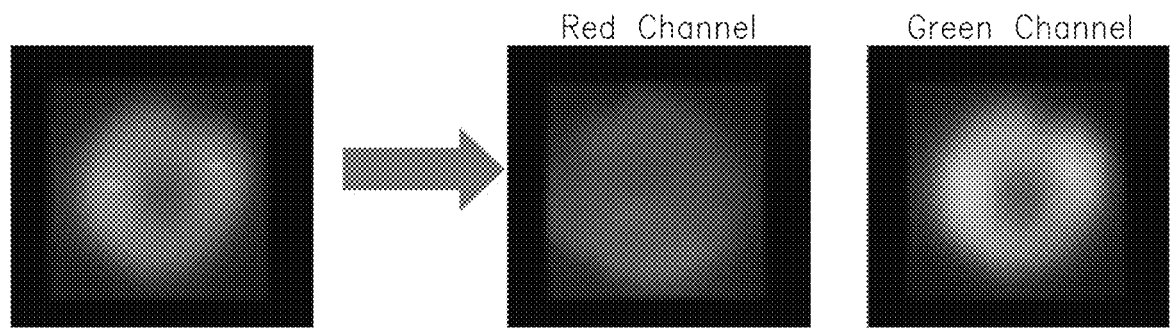
FIGS. 25A and 25B are images illustrating the differences between the intensity of a group of pixels disposed within an inner part of a Cell and the intensity of a group of pixels disposed within an outer part of a Cell, for both the red and green fluorescent images.
Figure 25B:
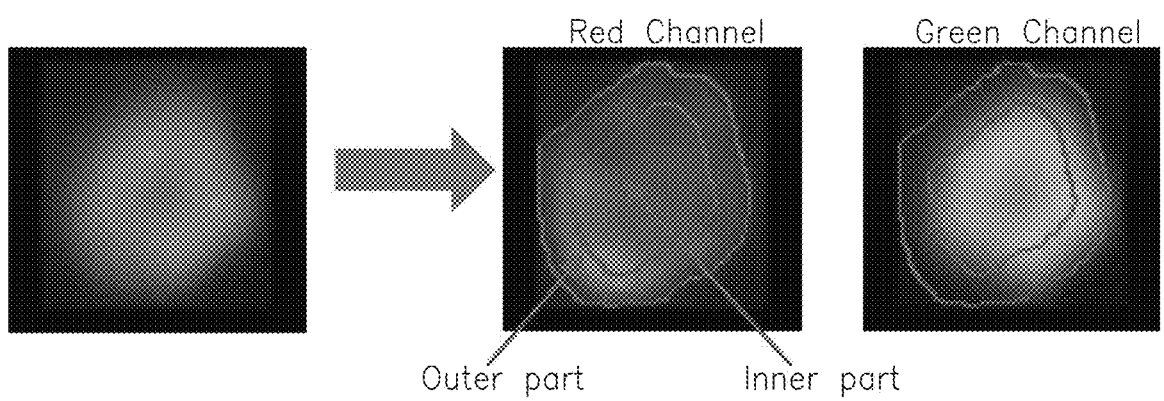
Figure 26:
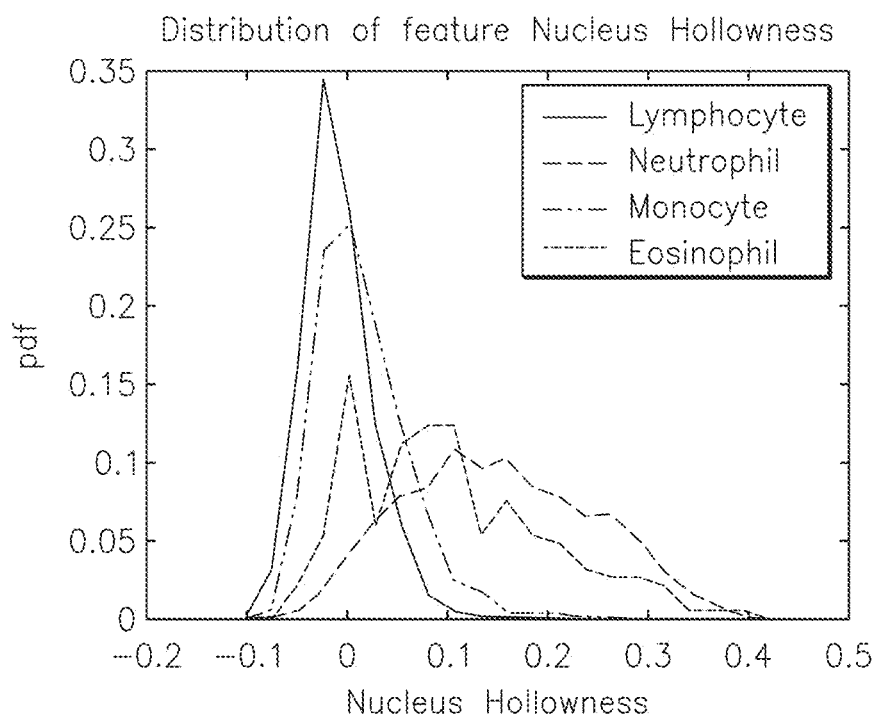
FIG. 26 is a graph depicting empirical data (in the form of a pdf) collected from a training set for each of lymphocytes, neutrophils, eosinophils, and monocytes, versus the Nucleus Hollowness for each of the aforesaid WBCs.

"Nucleus Hollowness" is an identifying feature that can be used in addition to, or in place of Nucleus Texture. Nucleus Hollowness is a ratio of the intensity (i.e., a quantifiable value) of a group of pixels disposed within the inner part of a Cell versus the intensity (i.e., a quantifiable value) of a group of pixels disposed on the outer part of the Cell in the fluorescent green image. The definition of what is the "outer part" and what is the "inner part" can be varied to suit the application at hand; e.g., based on empirical data. For example, the outer part can be defined as a band of a few pixels located at the boundary of the Cell; e.g., a band of three pixels at the boundary of the Cell when the pixel size is around 0.5 μm. The inner part would then be that area within the Cell other than the outer part. FIG. 25A includes the cell nucleus in the green channel to illustrate the differences in intensity between inner part and outer part of a Nucleus. FIG. 25B contains similar images, and includes encircling lines to facilitate the identification of the inner and outer parts. The relative intensities of the pixels of the inner and outer groups are such that the intensity of the inner pixels is typically quantifiably less than that of the outer pixels in some of the Neutrophils. FIGS. 25A and 25B show green channel and red channel images, where 25A shows a dim part in the Nucleus which appears like a hole. FIG. 26 graphically illustrates the differences in the "Nucleus Hollowness" associated with lymphocytes, neutrophils, monocytes, and eosinophils. The "Nucleus Hollowness" associated with Neutrophils, for example, has larger values than other types of cells and makes it an identifying feature that can be used to distinguish Neutrophils.

Figure 27:
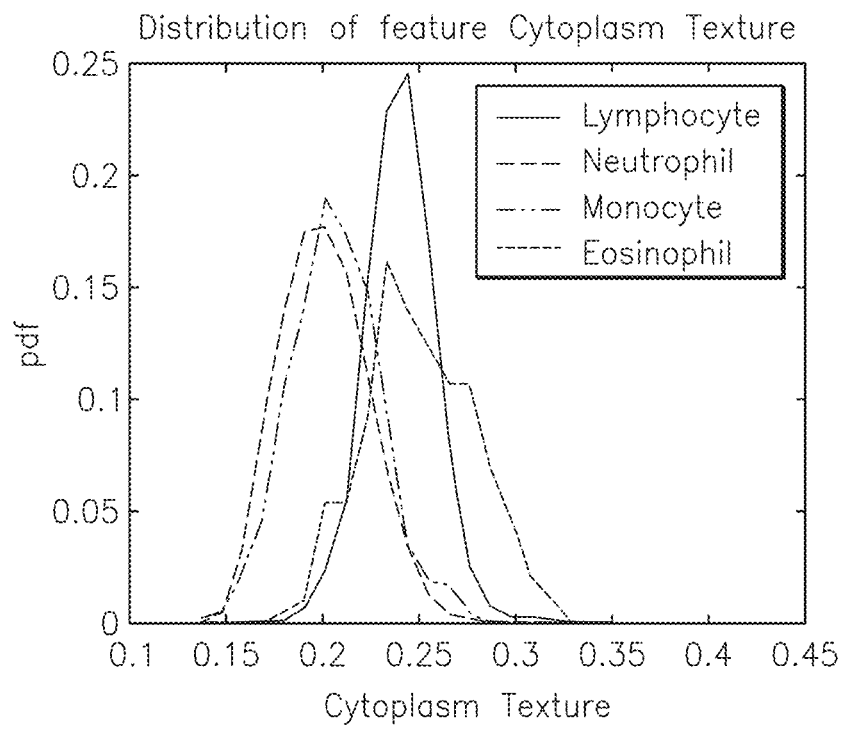
FIG. 27 is a graph depicting empirical data (in the form of a pdf) collected from a training set for each of lymphocytes, neutrophils, eosinophils, and monocytes, versus the Cytoplasm Texture for each of the aforesaid WBCs.

"Cytoplasm Texture" is an identifying feature that quantifies the "texture" of the fluorescent red light emitted within the cytoplasm of a Cell. The term "texture" is used to refer to the variability of the fluorescent red light within the cytoplasm of a Cell, typically on a per pixel basis. Several different techniques can be used to quantify the Cytoplasm Texture. For example, the standard deviation of the mean normalized red intensity value per pixel can be used to quantify the Cytoplasm Texture. Normalized fluorescent red intensity values can be determined by identifying all of the pixels within a Cell that emit fluorescent red light, and assigning an arbitrary value of zero to the pixels with the lowest intensity and a value of one to the pixels of the highest intensity. The standard deviation of the intensity values can be computed from those values using known techniques. FIG. 27 graphically illustrates the differences in the Cytoplasm Texture associated with lymphocytes, neutrophils, monocytes, and eosinophils. The Cytoplasm Texture associated with neutrophils, for example, makes Nucleus Texture an identifying feature that can be used to distinguish neutrophils.

Figure 28:
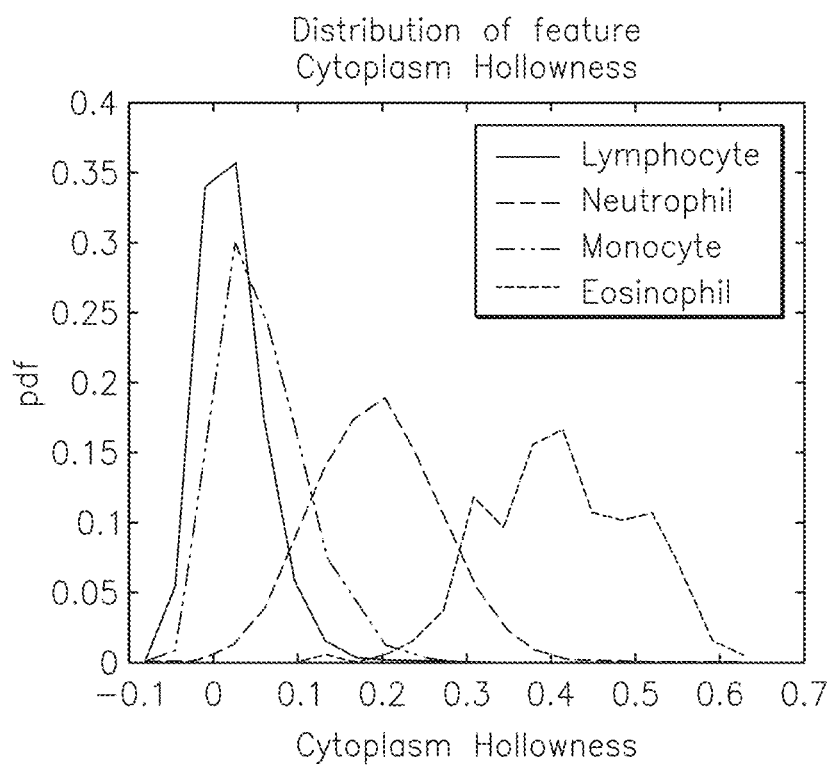
FIG. 28 is a graph depicting empirical data (in the form of a probability density function—pdf) collected from a training set for each of lymphocytes, neutrophils, eosinophils, and monocytes, versus the Cytoplasm Hollowness for each of the aforesaid WBCs.

In a manner similar to that described above vis-à-vis Nucleus Texture and Nucleus Hollowness, "Cytoplasm Hollowness" is an identifying feature that can be used in addition to, or in place of Cytoplasm Texture. Cytoplasm Hollowness is a ratio of the intensity (i.e., a quantifiable value) of a group of pixels disposed within the inner part of a cytoplasm versus the intensity of a group of pixels disposed on the outer part of the cytoplasm in the fluorescent red image. The relative intensities of the pixels of inner and outer groups are such that the intensity of the inner pixels is typically quantifiably less than that of the outer pixels in the Neutrophils and Eosinophils. FIG. 28 graphically illustrates the differences in the "Cytoplasm Hollowness" associated with lymphocytes, neutrophils, monocytes, and eosinophils. The "Cytoplasm Hollowness" associated with neutrophils, for example, is greater than that associated with lymphocytes and monocytes, but less than that associated with eosinophils, thus make it an identifying feature that can be used to distinguish neutrophils.

"Cell Absorption Texture at a Given Wavelength" is an identifying feature that quantifies the texture of the OD values of a Cell associated with blue light at a given wavelength transmitted through the Cell, which OD is sensed on a per pixel basis. As indicated above, the transmitted blue light can be in the range of about 405-425 nm, and transmitted blue light at about 413 nm is advantageous because at or about 413 nm is where hemoglobin has peak absorption. The "texture" refers to the variability of the OD values within the Cell. Also as indicated above, several different techniques can be used to quantify the texture; e.g., the standard deviation of the OD values associated with blue light at 413 nm. FIG. 29 graphically illustrates the differences in the Cell Absorption Texture at 413 nm associated with lymphocytes, neutrophils, monocytes, and eosinophils. The Cell Absorption Texture at 413 nm associated with eosinophils, for example, makes Cell Absorption Texture at 413 nm an identifying feature that can be used to distinguish eosinophils.

The above description of each of the features indicates a quantifiable value with which that feature of the cell can be evaluated. The present invention is not limited to the specifically identified form of the quantifiable value. For example, the Red-Green Ratio is described as a ratio of the mean intensity value of those pixels (or area) within an identified Cell depicting fluorescent red light, over the mean intensity value of those pixels (or area) within the identified Cell depicting fluorescent green light. As indicated by the "or area" in parentheses, the Red-Green Ratio could be described in terms of area, or ratio of pixels (each representing an area within the sample image), within which area the intensity values of the respective light meets a predetermined threshold.

As indicated above, the programmable analyzer is adapted to utilize identifying features, such as those described above, within an algorithm to perform the LDC. The quantitative information provided by the aforesaid features can be processed in a number of different ways to provide the information associated with an LDC.

In some embodiments, for example, the programmable analyzer is adapted to include a rule based classifier that evaluates the sample image relative to one or more of the features and use such evaluation to classify Cells within the sample. As indicated above, each feature is describable in terms of a quantitative value. Some or all of the Cells within the sample image are evaluated in terms of a feature; i.e., a quantitative value for that feature is determined from the sample image. The determined quantitative value is then evaluated relative to (e.g., compared against) a reference value for that feature for the purpose of determining whether or not that Cell is a particular type of WBC. The process of determining a quantitative value and comparing it to a reference value is followed for each type of feature under consideration (e.g., depending upon the analysis at hand, some analyses may not consider all of the features). For example, to evaluate a particular Cell image, the classifier may first consider the Cell Area feature. If the determined Cell Area value is below a predetermined cell area value (e.g., 60), the rule applied by the classifier could specify that certain WBC types are excluded and others are included; e.g., see FIG. 14 where lymphocytes show an area below 60 in the pdf and eosinophils, monocytes, neutrophils each have an area above 60. The term "excluded" is used herein to mean statistically not likely, and the term "included" to mean the converse—statistically likely. Next, the rule based classifier may evaluate the Cell image to determine the number of Lobes. If the determined number of Lobes is equal to or greater than a predetermined value (e.g., two), then the rule applied by the classifier would specify that certain WBC types are excluded and others are still included; see FIG. 13 which shows the probability for a Cell to have two or more Lobes is higher for monocytes and neutrophils than it is for lymphocytes, but still substantially higher for eosinophils). Next, the rule based classifier may evaluate the Cell image to determine a quantitative value for the Average Cell Absorption at a Given Wavelength. If the determined Average Cell Absorption value at the Given Wavelength (e.g., at 413 nm) is greater than a predetermined threshold value (e.g., about 215), then the rule applied by the classifier would specify that certain WBC types are excluded and others are still included; e.g., see FIG. 23 which illustrates that above a value of about 215, neutrophils, monocytes, and lymphocytes can be excluded, and only eosinophils can be included. Thus, by determining a quantitative value for each feature under consideration, and subsequently evaluating those values using certain rules, the rule based classifier makes a quantitative-based determination as to the WBC type; i.e., eosinophils.

The quantitative value of each identifying feature for a type of WBC will likely vary, to some degree, within a sample population from a particular subject, and may also vary between subjects. The present invention addresses this variability by, for example, utilizing a plurality of features to evaluate a Cell image. By using more than one feature to evaluate and identify a Cell, the present method decreases the potential for any particular feature to have an adverse effect on the accuracy of the evaluation. The table provided in FIG. 30 illustrates groups of dominant distinguishing features associated with particular types of WBCs. These feature groupings are examples of groups that can be used to significantly distinguish one WBC from another WBC within the four-part LDC. The variability can also be addressed by selectively adjusting the magnitude of the quantitative reference value(s) associated with each feature.

Figure 31:
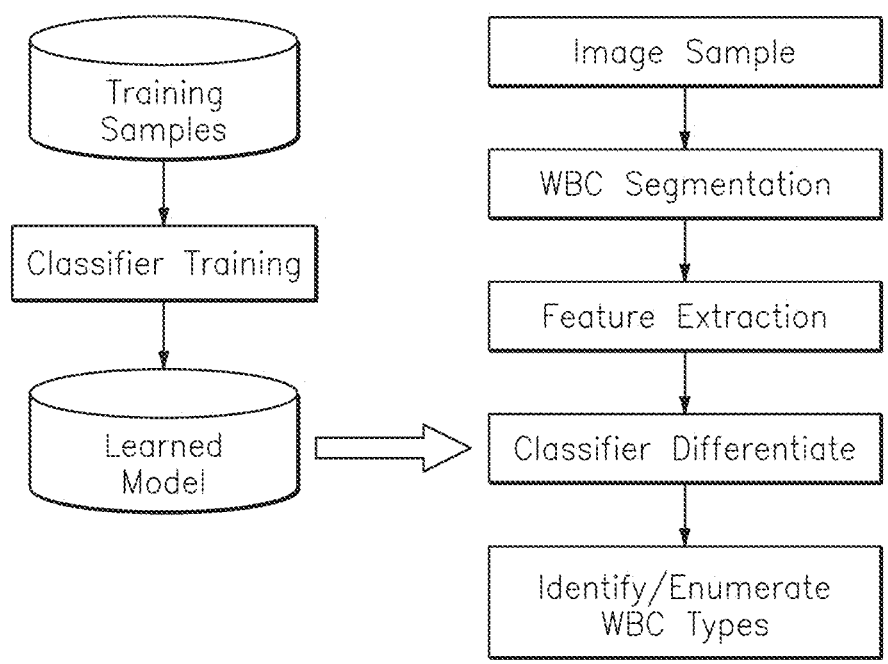
FIG. 31 is a flow chart illustrating a learned model embodiment of the present invention.

In some embodiments, the programmable analyzer is adapted to include a learned model based classifier. FIG. 31 is a flow chart that illustrates an example of processes associated with the learned model based classifier. As can be seen from the chart, training sample images are used to train the classifier, and the trained classifier in turn builds the learned model. Once the learned model is developed, that model is then utilized to evaluate features (e.g., such as those described above) associated with a Cell image from a sample, and to classify the Cell as a particular type of WBC based on those features.

Figure 32:
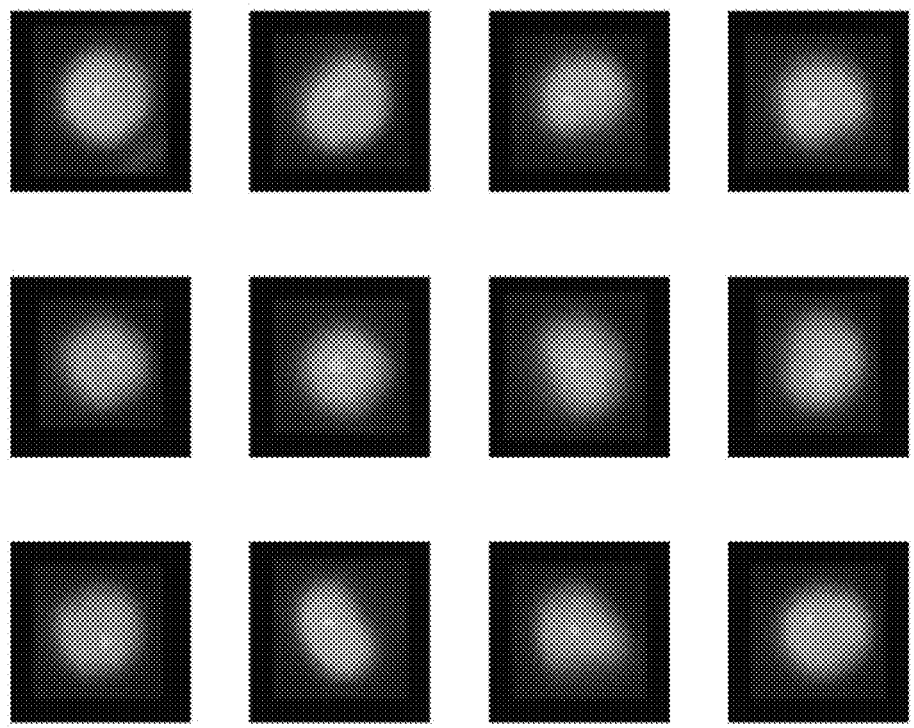
FIG. 32 is a group of twelve images of lymphocytes illustrative of a training set.
Figure 33:
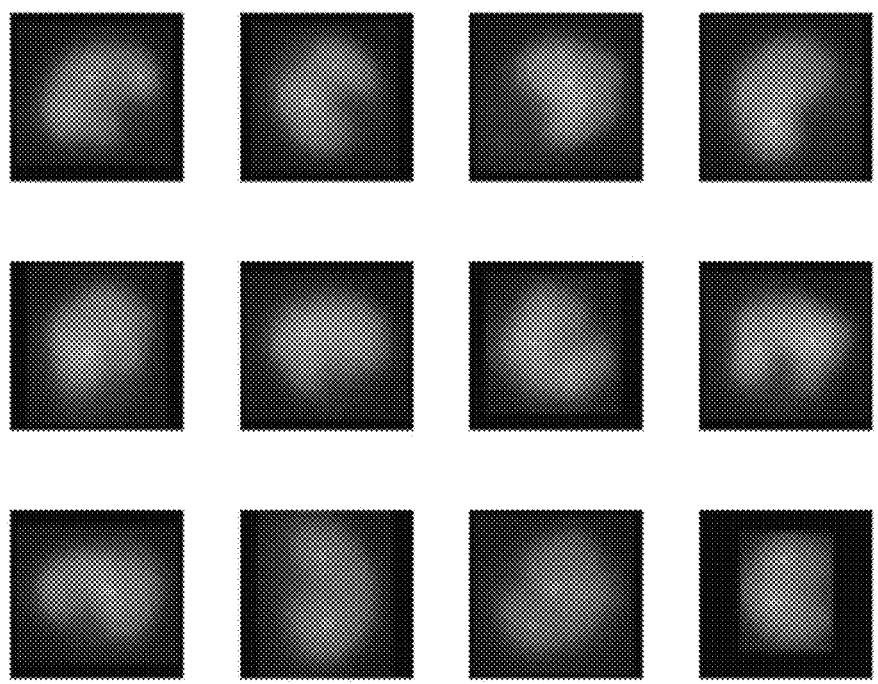
FIG. 33 is a group of twelve images of monocytes illustrative of a training set.
Figure 34:
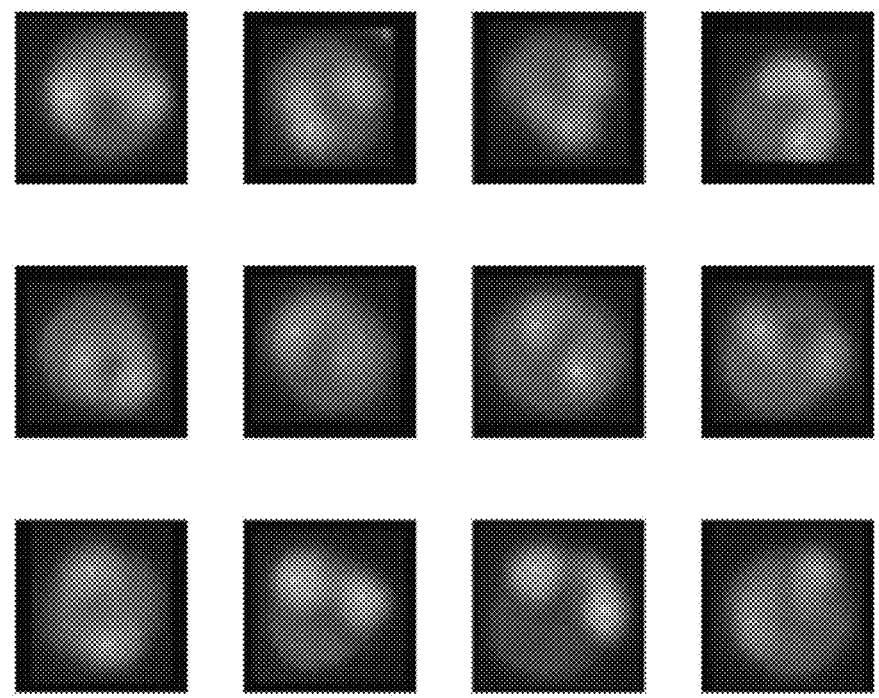
FIG. 34 is a group of twelve images of eosinophils illustrative of a training set.
Figure 35:
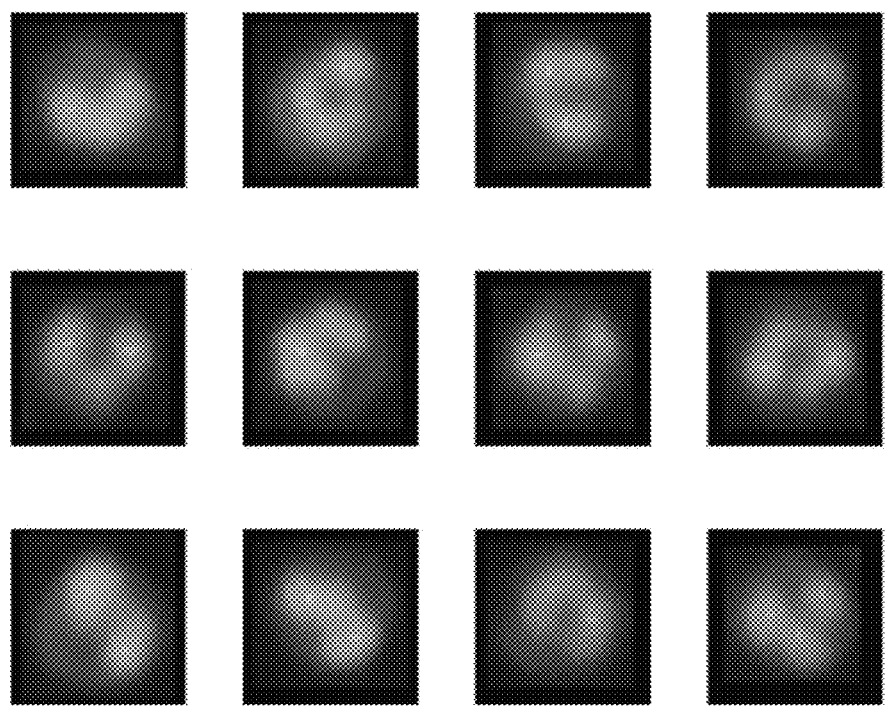
FIG. 35 is a group of twelve images of neutrophils illustrative of a training set.

The training sample images can be empirically collected (e.g., by a skilled technician) for each type of WBC identifiable within the LDC. For example, FIG. 32 illustrates twelve lymphocyte images from the training set, and FIGS. 33, 34, and 35 illustrate examples in the training sets for each of monocytes, eosinophils, and neutrophils, respectively. The number of cell images in each set is selected to provide sufficient data for each WBC type for training purposes; i.e., sufficient data to enable the classifier to be trained with an acceptable level of accuracy for the analysis type. The learned model used within this embodiment is not limited to any particular size training set. Often a training set can contain hundreds to thousands of each type of WBCs to faithfully represent the variability within different people, different imaging conditions and etc.

The classifier can be trained (and the learned model developed) by quantitatively evaluating each Cell image within a training set to determine a quantitative reference value(s) for each feature for each Cell, and then determine a collective quantitative reference value for each feature for the training set (or a statistical representation of reference values; e.g., a probability density function). The collective reference values (or statistical representations thereof) can then be used to build the learned model. FIGS. 13, 14, 16-18, 21-24, and 26-29 graphically depict probability density functions associated with each feature based on training sets, for lymphocytes, monocytes, eosinophils, and neutrophils relative to that feature. The learned models permit the present application to adjust based on actual image data, and the automated interpretation of that image data, and thereby provide a desirable level of accuracy.

The present invention is not limited to any particular type of learned model. Examples of acceptable types of learned models include a statistical model such as a Bayesian classifier, a linear model such as a Support Vector Machine (SVM), and a neural network model such as a Multilayer Perceptron. In terms of the Bayesian classifier model, a Bayesian model can be implemented utilizing the probability density functions described above for each feature to compute a posterior distribution for each of the WBC types. Each posterior distribution describes the conditional probability of an event (e.g., the occurrence of a particular WBC)

after the relevant evidence (e.g., the computed features) is taken into consideration. The Bayesian model then evaluates the posterior distributions to determine which of the WBCs has the greatest posterior distribution. The Cell image under evaluation is then labeled as being the same type as the WBC having the greatest posterior distribution. Bayesian probability modeling is well known and the present invention is not limited to any particular mathematical techniques associated with Bayesian modeling. An example of a text that describes Bayesian modeling in detail is "Pattern Classification" by R. O. Duda, P. E. Hart, and D. G. Stork, John Wiley & Sons, 2001, and which is hereby incorporated by reference in its entirety.

The Support Vector Machine ("SVM") is a linear classifier that utilizes the training samples developed for the features and organizes them to determine if the data is linearly separable in n-dimensional space. If the data is linearly separable by a (n−1)-dimensional hyper-plane extending between the feature data groups, then the data can be classified by virtue of its position relative to the hyper-plane. An optimum position of the hyper-plane can be selected relative to the data by using support vectors aligned with data points from each data group. Once an optimum hyper-plane position is determined (i.e., the position where the margin between the hyper-plane and the closest data points/support vectors is largest), then the position of the hyper-plane becomes the mechanism for distinguishing between WBCs; i.e., data points residing on one side of the hyper-plane are associated with a particular type of WBC and data points residing on the other side of the hyper-plane are associated with another type of WBC. In terms of an SVM, the hyper-plane may be considered to be a two, three dimensional or higher dimensional "reference value". In certain instances where the probability information is not linearly separable, it is sometimes possible to use a data manipulation technique (typically referred to as a "kernel trick") in which the data can be reorganized using a non-linear function (e.g., a polynomial or RBF kernel function). The reorganized data permits the positioning of the hyper-plane, and consequent determination of WBC type. SVM type classifiers are well known and the present invention is not limited to any particular embodiment thereof. An example of a text that describes SVM type classifiers in detail is "A Training Algorithm for Optimal Margin Classifiers", B. E. Boser, I. M. Guyon, and V. N. Vapnik, In D. Haussler, editor, $5^{th}$ Annual ACM Worshop on COLT, pgs. 144-152, Pittsburgh, Pa., 1992, ACM Press, and "A Tutorial on Support Vector Machines for Pattern Recognition", C. J. C. Burges, Data Mining and Data Knowledge Discovery 2: 121-167, 1998, each of which is hereby incorporated by reference in its entirety.

As indicated above, the present invention is not limited to using any particular learning model. In some instances, combinations of models can be used. For example, a rule-based classifier may be implemented in certain applications to make an initial organization of the data. The remaining data may be analyzed using a learning model such as the above-described SVM model.

In the operation of the invention, an undiluted fluid sample of whole blood is collected into a disposable cartridge such as that illustrated in FIG. 3. Reagents, including one or more colorants (e.g., ACO) and an anticoagulant (e.g., EDTA), are added to the fluid sample to facilitate the LDC analysis. The fluid sample admixed with the reagents is deposited within the analysis chamber portion of the cartridge, where it quiescently resides during the imaging process. The cartridge is inserted into (or otherwise engaged with) the analysis device, where it is appropriately positioned by the cartridge holding and manipulating device relative to the objective lens, sample illuminator, and image dissector, and is subsequently imaged.

In most instances, the analysis device is programmed to image the entirety of the fluid sample quiescently residing within the chamber. In some applications, however, a portion of the fluid sample can be imaged. The imaging process can vary depending upon the application at hand. For the four-part LDC described above, the imaging process involves subjecting the sample to a fluorescent excitation light source (e.g., light at about 470 nm from the epi-fluorescent light source), and to a transmission light source (e.g., blue light at or about 413 nm). The excitation light source causes the colorant combined with elements disposed within the fluid sample to emit fluorescent light at two different wavelengths (e.g., red ~660 nm, and green ~540 nm). Some amount of the transmitted light passes through the fluid sample, and the remainder is absorbed by the sample/colorant. The image dissector captures the light transmitted through the fluid sample and fluorescing from the fluid sample and provides signals representative of the intensity and color of the captured light. The signals are processed into a form that permits the programmable analyzer to form an image of the sample based on the signals, which image can be quantitatively analyzed to perform the four-part LDC.

As indicated above, in some embodiments of the present invention the programmable analyzer is adapted with an algorithm that includes a learned model. The model is developed using training sets and once developed can be used to accurately identify WBCs within the sample, and classify the WBCs as lymphocytes, monocytes, eosinophils, or neutrophils. The algorithm (including those that utilize a learned model) in a particular analysis device can be provided from a master copy and downloaded into the programmable analyzer of that particular analysis device.

Referring to FIGS. 30 and 31, during the quantitative analysis of the sample image, the algorithm identifies WBCs within the image. To facilitate and/or expedite the analysis, the sample image can be masked (e.g., by segmentation) to eliminate all the sample image except those portions identified as a Cell. The image portions identified as Cells are then quantitatively evaluated in terms of one or more of the features (e.g., see feature groupings disclosed in FIG. 30), and typically in terms of substantially all of the features. The quantitative values (or probability density functions) for each of the Cells for each of the features are then utilized within the algorithm (e.g., the learned model portion) to classify the Cells. Once the Cells are classified and enumerated, the data is organized to provide the LDC data.

Preliminary investigation into the accuracy of the present method and apparatus indicates a high degree of accuracy. The preliminary investigation utilized samples from a population of sixty-two subjects, and compared the WBC identification results determined using the present invention for each of the samples, versus sample analysis results prepared by a trained hematologist manually examining the samples. A set of 500-1000 cells were evaluated from each sample. A linear regression analysis of the two analyses of the samples indicates that for neutrophils, lymphocytes, monocytes, and eosinophils, the $R^2$ values show close agreement between the manual analysis results and the results from an analysis device according to the present invention.

Although this invention has been shown and described with respect to the detailed embodiments thereof, it will be understood by those skilled in the art that various changes in form and detail thereof may be made without departing from the spirit and the scope of the invention.

What is claimed is:

1. A method for identifying at least one type of white blood cell (WBC) within a whole blood sample, comprising:
   adding at least one colorant to the whole blood sample, which colorant is operable to differentially identify at least one WBC type from another WBC type;
   disposing the blood sample into a chamber;
   providing at least one fluorescent excitation light and at least one transmission light;
   receiving both light fluorescing from the sample and light transmitted through the sample and producing signals representative of the fluorescence and transmittance of the received light;
   creating at least one image of the sample quiescently residing within the chamber using said signals;
   identifying WBCs within the sample image;
   quantitatively analyzing at least some of the identified WBCs within the image, including determining one or more quantitative values representative of one or more predetermined quantitatively determinable features, wherein each quantitative value is based on one or more values of light intensity, light color, optical density, area or geometric shape, and comparing each quantitative value against a reference value; and
   identifying at least one type of WBC within the identified WBCs based on the plurality of predetermined quantitatively determinable features, the determined quantitative values, and the comparison of each quantitative value against its reference value;
   wherein the one or more predetermined quantitatively determinable features include one or more of average cell absorption at a given wavelength, cell absorption texture at the given wavelength, cell area, or nucleus area.

2. The method of claim 1, wherein the one or more predetermined quantitatively determinable features include one or more of number of lobes, ratio of large granules, ratio of nucleus, red-green ratio, nucleus brightness, and cytoplasm brightness.

3. The method of claim 1, wherein the one or more predetermined quantitatively determinable features include one or more of average cell absorption at a given wavelength, cell absorption texture at the given wavelength, cell area, or nucleus area.

4. The method of claim 1, wherein the one or more predetermined quantitatively determinable features include one or both of nucleus texture and cytoplasm texture, and wherein the quantitatively determinable feature of nucleus texture includes the steps of quantifying fluorescent green intensity values within a nucleus and determining a deviation of those determined fluorescent green intensity values; or
   wherein the quantitatively determinable feature of cytoplasm texture includes the steps of quantifying fluorescent red intensity values within cytoplasm in a WBC and determining a deviation mean of those determined fluorescent red intensity values.

5. The method of claim 1, wherein the one or more predetermined quantitatively determinable features include one or both of nucleus hollowness and cytoplasm hollowness.

6. The method of claim 1, wherein the step of identifying at least one type of WBC from the identified WBCs includes identifying one or more of lymphocytes, neutrophils, monocytes, and eosinophils.

7. The method of claim 6, wherein lymphocytes are identified using one or more features from a group consisting of: number of lobes, cell area, ratio of nucleus and nucleus shape.

8. The method of claim 6, wherein neutrophils are identified using one or more features from a group consisting of: number of lobes, cell area, ratio of nucleus and nucleus shape.

9. The method of claim 6, wherein monocytes are identified using one or more features from a group consisting of: number of lobes, cell area, and ratio of nucleus.

10. The method of claim 6, wherein eosinophils are identified using one or more features from a group consisting of: said average cell absorption at a given wavelength, said cell absorption texture at a given wavelength, and ratio of large granules.

11. An apparatus for identifying at least one type of white blood cell (WBC) within a whole blood sample, comprising:
    a sample illuminator configured to provide at least one fluorescent excitation light and at least one transmission light;
    an image dissector configured to detect light fluorescing from the sample and light transmitted through the sample and produce signals representative of the fluorescence and transmittance of the received light;
    a programmable analyzer in communication with the sample illuminator, the image dissector, and with stored executable instructions, which instructions when executed cause the analyzer to:
    create at least one image of the sample quiescently residing within the chamber using said signals;
    identify WBCs within the at least one sample image;
    quantitatively analyze at least some of the identified WBCs within the at least one image, including determining one or more quantitative values representative of one or more predetermined quantitatively determinable features, wherein each quantitative value is based on one or more values of light intensity, light color, optical density, area or geometric shape, and comparing each quantitative value against a reference value; and
    identify at least one type of WBC within the identified WBCs based on the plurality of predetermined quantitatively determinable features, the determined quantitative values, and the comparison of each quantitative value against its reference value;
    wherein the one or more predetermined quantitatively determinable features include one or more of average cell absorption at a given wavelength, cell absorption texture at the given wavelength, cell area, or nucleus area.

12. A method for identifying at least one type of white blood cell (WBC) within an undiluted whole blood sample, the sample including at least one colorant that is operable to differentially identify at least one WBC type from another WBC type, the method comprising:
    disposing the blood sample into a chamber;
    providing at least one fluorescent excitation light and at least one transmission light;
    receiving both light fluorescing from the sample and light transmitted through the sample and producing signals representative of the fluorescence and transmittance of the received light;
    separating the signals into a plurality of emittance channels for light fluorescently emitted from the sample quiescently residing within the chamber, the plurality of emittance channels including a first emittance channel for light emitted from the sample at a first wavelength, and a second emittance channel for light emitted from the sample at a second wavelength, which first wavelength is different than said second wavelength, and a plurality of transmittance channels for light transmitted through the sample quiescently residing within the chamber, the plurality of transmittance channels including a first transmittance channel for light transmitted through the sample at a third wavelength, and a second transmittance channel for light transmitted through the sample at a fourth wavelength, which third wavelength is different than said fourth wavelength;

quantitatively analyzing at least one WBC within the sample, including determining one or more quantitative values using the signals separated into the plurality of emittance channels and the plurality of transmittance channels; and identifying the type of the at least one WBC based on the one or more quantitative values.

13. The method of claim 12, wherein the quantitatively analyzing the at least one WBC within the sample further includes comparing at least one of the one or more quantitative value against a respective reference value.

14. The method of claim 13, wherein the identifying the type of at least one type of WBC uses the comparison of the at least one of the one or more quantitative value against the respective reference value.

15. The method of claim 12, wherein the one or more quantitative values are representative of one or more predetermined quantitatively determinable features; and the one or more predetermined quantitatively determinable features include one or more of number of lobes, ratio of large granules, ratio of nucleus, red-green ratio, nucleus brightness, and cytoplasm brightness.

16. The method of claim 12, wherein the one or more quantitative values are representative of one or more predetermined quantitatively determinable features; and the one or more predetermined quantitatively determinable features include one or more of average cell absorption at a given wavelength, and cell absorption texture at the given wavelength.

17. The method of claim 12, wherein the one or more quantitative values are representative of one or more predetermined quantitatively determinable features; and the one or more predetermined quantitatively determinable features include one or both of cell area and nucleus area.

* * * * *